(12) United States Patent
Khait et al.

(10) Patent No.: US 12,232,438 B2
(45) Date of Patent: Feb. 25, 2025

(54) SYSTEM AND METHOD FOR REAL-TIME CROP MANAGEMENT

(71) Applicant: Centure Applications LTD, Tel Aviv (IL)

(72) Inventors: Itzhak Khait, Kibbutz Ein Zivan (IL); Moshe Bar, Rishon Le-Zion (IL)

(73) Assignee: Centure Applications LTD, Tel Aviv (IL)

( * ) Notice: Subject to any disclaimer, the term of this patent is extended or adjusted under 35 U.S.C. 154(b) by 0 days.

(21) Appl. No.: 18/810,722

(22) Filed: Aug. 21, 2024

(65) Prior Publication Data

US 2024/0423113 A1 Dec. 26, 2024

Related U.S. Application Data

(63) Continuation of application No. 17/758,439, filed as application No. PCT/IL2020/051206 on Nov. 23, 2020.

(Continued)

(51) Int. Cl.
*G06T 7/00* (2017.01)
*A01B 79/00* (2006.01)
(Continued)

(52) U.S. Cl.
CPC ............ *A01B 79/005* (2013.01); *A01B 79/02* (2013.01); *C12N 15/8212* (2013.01);
(Continued)

(58) Field of Classification Search
CPC .................. A01B 79/005; A01B 79/02; C12N 15/8212; C12N 15/8213; G06T 7/0002; G06T 2207/10032; G06T 2207/30188
See application file for complete search history.

(56) References Cited

U.S. PATENT DOCUMENTS 9,148,995 B2 10/2015 Hmicek et al.
10,255,670 B1 4/2019 Wu et al.
(Continued)

FOREIGN PATENT DOCUMENTS

CN 108684644 A 10/2018
EP 2505652 B1 10/2015
(Continued)

OTHER PUBLICATIONS

Graeff, S., et al. "Evaluation of different active and passive sensor systems to adapt N fertilizer applications in broccoli (*Brassica oleracea* convar. *botrytis* var. *italica*)." International Symposium on Application of Precision Agriculture for Fruits and Vegetables 824. Dec. 31, 2008.

(Continued)

*Primary Examiner* — Mathew Franklin Gordon
(74) *Attorney, Agent, or Firm* — Intrinsic Law Corp.

(57) ABSTRACT

The present invention discloses a method for selective crop management in real time. The method comprises steps of: (a) producing a biosensor plant, said biosensor plant comprises a visual biomarker, said biomarker is encoded by at least one modified genetic locus comprising (i) preselected reporter gene allele having a phenotype detectable by a sensor, and (ii) a regulatory region of a preselected gene allele responsive to at least one parameter or condition of said plant or its environment, said regulatory region is operably linked to said reporter gene, such that the expression of said reporter gene phenotype is correlated with the status of said at least one parameter or condition of said biosensor plant or its environment; (b) acquiring image data of a target area comprising a plurality of said biosensor plants via said sensor and processing said data to generate a signal indicative of the phenotypic expression of said reporter gene allele of said biosensor plant; and (c) com- (Continued)

municating said signal to an execution unit communicably linked to the sensor, said execution unit is capable of exerting in real time a selective monitoring and/or treatment of said target area or a portion thereof comprising said biosensor plants, said treatment is being responsive to said status of said parameter or condition of the biosensor plant or its environment. The present invention further discloses systems and plants related to the aforementioned method.

20 Claims, 15 Drawing Sheets

Related U.S. Application Data

(60) Provisional application No. 63/060,834, filed on Aug. 4, 2020, provisional application No. 62/960,880, filed on Jan. 14, 2020.

(51) Int. Cl.
*A01B 79/02* (2006.01)
*C12N 15/82* (2006.01)

(52) U.S. Cl.
CPC ........ *C12N 15/8213* (2013.01); *G06T 7/0002* (2013.01); *G06T 2207/10032* (2013.01); *G06T 2207/30188* (2013.01)

(56) References Cited

U.S. PATENT DOCUMENTS

| | | | |
|---|---|---|---|
| 11,393,049 | B2 | 7/2022 | Khait et al. |
| 2004/0195356 | A1 | 10/2004 | Ellsworth |
| 2012/0237083 | A1 | 9/2012 | Lange et al. |
| 2018/0330166 | A1 | 11/2018 | Redden et al. |
| 2019/0064363 | A1 | 2/2019 | Redden et al. |
| 2019/0124827 | A1 | 5/2019 | Davis et al. |
| 2019/0239502 | A1 | 8/2019 | Palomares et al. |
| 2020/0011019 | A1 | 1/2020 | Serrat et al. |
| 2020/0214281 | A1 | 7/2020 | Koch |
| 2020/0406281 | A1 | 12/2020 | Funseth et al. |

FOREIGN PATENT DOCUMENTS

| | | |
|---|---|---|
| GB | 2551345 A | 12/2017 |
| KR | 20100034808 A | 4/2010 |
| WO | 2020049576 A2 | 3/2020 |
| WO | 2022064482 A1 | 3/2022 |
| WO | 2022172274 A1 | 8/2022 |

OTHER PUBLICATIONS

R. Booker, "Technology targets spray control", WEEDit Blog (Mar. 22, 2018).
Klein et al., "Nozzles—Selection and Sizing", Cooperative Extension, Institute of Agricultural & Natural Resources at the University of Nebraska—Lincoln cooperating with the Counties and the USDA, EC141 p. 1-10, The Board of Regents of the University of Nebraska (2011).
T. Wolf, "Optical Spot Spraying and AI Scouting", Sprayers 101 (Feb. 8, 2018).
ISA/US, International Search Report and the Written Opinion of the International Searching Authority in re Int'l App. No. PCT/IL2021/051133 (Dec. 22, 2021).
ISA/IL, International Search Report and the Written Opinion of the International Searching Authority in re Int'l App. No. PCT/IL2022/050174 (May 17, 2022).

Untreated plant → Treated plant not in N deficit → Treated plant in with N deficit & activated visual marker

| PLASTIC GENERAL TOLERANCE | | |
|---|---|---|
| over | incl | |
| 0 | 6 | ±0.1 |
| 6 | 30 | ±0.3 |
| 30 | 120 | ±0.6 |
| 120 | 315 | ±1.5 |
| 315 | 1000 | ±4.0 |
| angle | | ±3° |

FIG. 15

SYSTEM AND METHOD FOR REAL-TIME CROP MANAGEMENT

CROSS-REFERENCE TO RELATED APPLICATIONS

This application is a continuation of U.S. application Ser. No. 17/758,439, filed on Jul. 6, 2022, which is a national stage application of PCT/IL2020/051206, filed on Nov. 23, 2020, which claims priority to U.S. Provisional Application No. 62/960,880, filed on Jan. 14, 2020, and to U.S. Provisional Application No. 63/060,834, filed on Aug. 4, 2020, which are hereby incorporated by reference.

FIELD OF THE INVENTION

The present invention relates generally to the field of precision agriculture and particularly to precision agriculture techniques for real-time monitoring and treatment of the plant or its environment condition. More specifically, the current invention relates to plants expressing biosensors for monitoring the plant or its environment condition.

BACKGROUND OF THE INVENTION

Precision agriculture is aimed at automated solutions for farm efficiency, increased yield and less waste. Precision agriculture uses data from multiple sources to improve crop yields and increase the cost-effectiveness of crop management strategies including fertilizer inputs, irrigation management, and pesticide and herbicide application.

Remote sensing has been promoted as a key source of information available in support of precision agriculture for decades. Recent technological developments, specifically the availability of high-resolution satellite imagery, and rapid development of unmanned aerial vehicle technology (UAV), suggest that adoption of remote-sensing data sources in precision agriculture is likely to rapidly increase in the coming decade. However, while these new evolving approaches have substantially enhanced phytomonitoring, the existing methods are still cumbersome, imprecise, require complex and expensive equipment and, in many cases, do not provide real-time monitoring and treatment of a crop's condition.

The use of sensors for monitoring the growth and development of plants is an increasing and useful practice to enhance the productivity and quality of food. The generation of high-quality food, with high nutraceutical or functional characteristics, is an increasing challenge, especially when the food is produced through environmental-care practices and low-cost concept in order to reduce the damage of the environment and increase the benefit to the growing population.

In precision agriculture, the use of sensors can help to create the optimal conditions to maximize the cost-effective production of crops with high nutraceutical quality through sustainability practices by incorporating suitable sensors based on different principles (e.g., electrical, chemical, optical and radiation, thermal, and biological). The sensors in precision agriculture should have the capacity of sensing and detecting chemical elements, biomolecules and variables related to vigor and sanity and must be able to communicate with processing units to extract the information of interest that could help to create the necessary conditions to maximize the production and nutraceutical characteristics of crops. However, this information is widely dispersed and it is not analyzed in a critical way to be integrated into a global practical technology that facilitate the different aspects of precision agriculture.

For example, U.S. Pat. No. 9,284,569 discloses transplastomic plant cell of a species of *petunia* or a species of *Nicotiana*, containing a LUX operon comprising LUX genes integrated within a plastidal genome. The LUX genes are separated by an intercistronic expression element (IEE) operably linked thereto and the expression of said LUX genes is enhanced by a heterologous translational leader sequence operably linked to one or more of the LUX genes. This publication further teaches that the images were taken using a BioRad ChemiDoc XRS Molecular Imager when the plants were grown in tissue culture magenta boxes. It is noted that U.S. Pat. No. 9,284,569 fails to show real-time selective treatment of the detected plants using advanced computational systems and algorithms.

U.S. Pat. No. 8,747,835 describes artificial DNA sequences incorporating LuxC and LuxE mutations, designed to further enhance light output of the LUX operon. The utility and applicability of the current invention includes, for example, generating bright autoluminescent plants. This is used for the production of plant biosensors emitting light in response to various types of stress or other conditions when operons containing these sequences are under the control of appropriate promoters, e.g., stress-inducible promoters, and are thus useful in agriculture for crop or environmental monitoring.

U.S. Pat. No. 7,408,145 discloses a light sensor for measuring the reflectance of an object, in particular the determination of plant status via remote sensing of plant biomass and plant biochemical properties for the purposes of mapping and applying agricultural products e.g. nitrogen based fertilizer. However, this publication does not teach the production and use of plants comprising biosensors selective treatment of the plants in real-time.

U.S. Pat. No. 9,030,549 discloses a method of distinguishing individual plants within a row of plants extending from a ground by illuminating two contiguous plants within the row at an angle between the ground and a normal vector to the ground with a light; collecting an image of the two plants with a camera; identifying a continuous region indicative of a plant; identifying points of interest within the region based on gradients identified within the region; and segmenting the region into a first and a second sub-region encompassing the first and the second selected points of interest, respectively. This publication does not teach or suggest monitoring and treatment of plants using plant biosensors that generate phenotypes detectable by remote sensors in real-time.

U.S. Pat. No. 9,510,586 describes a system for deactivating plant material outside of a growing region to prevent propagation of designated plant material outside of the growing region. The system comprises an imaging sensor configured to remotely detect plant material outside of the growing region; a vehicle including a sampling implement configured to collect a sample of plant material; a plant sensor configured to analyze the sample of plant material; a deactivation device configured to deactivate plant material; and a controller configured to direct the vehicle to the plant material detected by the imaging sensor, cause the sampling implement to collect the sample from the detected plant material, cause the plant sensor to analyze the sample, and, when the sample is determined to be designated for deactivation, cause the deactivation device to deactivate the detected plant material. However, the US patent teaches collecting of a sample of the plant in order to perform detection and analysis of the plant condition, which might damage the crop, in addition it is absent of teaching towards usage of artificial intelligence approaches.

U.S. Pat. No. 10,139,279 discloses a system for biosensing a state of crops of having a disease or not, using an unmanned aerial vehicle (UAV) equipped to collect hyperspectral images of a crop and at least one fog computer located near the crop connected wirelessly to exchange and process crop-related data in real-time. This publication does not teach usage of plants with biosensors generating phenotypes detectable by remote sensors in real-time.

In view of the above, there is still a long felt and unmet need for advanced precise agriculture systems and methods designed for monitoring and selective treatment of plants in real time.

SUMMARY OF THE INVENTION

It is one object of the present invention to disclose biosensor plants for smart and real time crop management application.

It is a further object of the present invention to disclose the method as defined above, wherein said method comprises steps of: (a) producing a biosensor plant, said biosensor plant comprises a visual biomarker, said biomarker is encoded by at least one modified genetic locus comprising (i) preselected reporter gene allele having a phenotype detectable by a sensor, (ii) a regulatory region of a preselected gene allele responsive to at least one parameter or condition of said plant or its environment, said regulatory region is operably linked to said reporter gene, such that the expression of said reporter gene phenotype is correlated with the status of said at least one parameter or condition of said biosensor plant or its environment; (b) acquiring image data of a target area comprising a plurality of said biosensor plants via said sensor and processing said data to generate a signal indicative of the phenotypic expression of said reporter gene allele of said biosensor plant; and (c) communicating said signal to an execution unit communicably linked to the sensor, said execution unit is capable of exerting in real time a selective monitoring and/or treatment of said target area or a portion thereof comprising said biosensor plants, said treatment is being responsive to said status of said parameter or condition of the biosensor plant or its environment.

It is a further object of the present invention to disclose the method as defined in any of the above, further comprises steps of (a) growing said biosensor plant or a plurality of said biosensor plants in the target area distributed in mixture with or in proximity to commercially valuable crop plants absent of said at least one modified genomic locus; (b) acquiring said image data of said target area comprising said biosensor plants distributed in mixture with said plurality of crop plants absent of said modified genomic locus; and (c) exerting in real time said selective treatment responsive to said status of said parameter or condition of the biosensor plant or its environment to at least a portion of the target area comprising said biosensor plants distributed in mixture with said plurality of crop plants absent of said modified genomic locus, said treatment is in direct or negative correlation with the expression of said visual marker in said biosensor plants.

It is a further object of the present invention to disclose the method as defined in any of the above, wherein said biosensor plant is a commercial or elite line, variety or strain, a cover crop plant, a hybrid or an inbred line.

It is a further object of the present invention to disclose the method as defined in any of the above, wherein said step of producing said biosensor crop plant comprising steps of:

(a) selecting a genomic locus within said comprising an allele of said reporter gene, said allele having a visual phenotype detectable by said sensor; and (b) modifying the regulatory region of said reporter gene allele within said genomic locus to comprise said preselected regulatory region responsive to the status of said at least one parameter or condition of said biosensor plant or its environment, such that the expression of said reporter gene is modulated by said regulatory region and correlated with said status of said at least one parameter or condition of said biosensor crop plant or its environment.

It is a further object of the present invention to disclose the method as defined in any of the above, wherein said method comprises steps of applying said treatment selectively to the biosensor plant in need according to the status of said parameter or condition of the biosensor crop plant or its environment detected by the sensor.

It is a further object of the present invention to disclose the method as defined in any of the above, wherein said signal is instructions for treatment positively or negatively correlated with the presence of said visual marker.

It is a further object of the present invention to disclose the method as defined in any of the above, wherein said method comprises steps of applying said treatment selectively to plants in proximity to the biosensor plant in need, according to the status of said parameter or condition of the biosensor crop plant or its environment detected by the sensor.

It is a further object of the present invention to disclose the method as defined in any of the above, wherein said reporter gene allele and/or said gene allele responsive to the at least one parameter or condition of said plant or its environment, is an endogenous or cisgeneic mutated allele.

It is a further object of the present invention to disclose the method as defined in any of the above, wherein said phenotype is a visually detectable phenotype.

It is a further object of the present invention to disclose the method as defined in any of the above, wherein said reporter gene phenotype is a visually detectable phenotypic characteristic, a visual marker, a biomarker or biosensor, detectable by said sensor predesigned or customized for detecting said phenotypic characteristic.

It is a further object of the present invention to disclose the method as defined in any of the above, wherein the phenotype of said reporter gene allele comprises shape, color, morphology, plant pigment, size, viability, smell, developmental stage, physiological state, phonological stage of plant growth, stress condition, nutrient status or deprivation, chlorophyll content, leaf morphology, colorization or veins structure, plant biomass, water content or status, disease condition and any combination thereof.

It is a further object of the present invention to disclose the method as defined in any of the above, wherein the reporter gene allele is selected from the group consisting of fluorescent proteins (FPs) such as green fluorescent protein (GFP), monomeric red and far-red FPs, reversible and irreversible photochromism in FPs, Infrared FPS (IFPs), non-fluorescent proteins such as chromoproteins (CPs), plant pigment molecules such as anthocyanins, carotenoids, flavonoids and betalain, absorbance and/or reflectance and/or fluorescence and/or spectral property of the plant, morphology changes such as epicuticular wax (e.g. Diketone wax) and trichomes; and any combination thereof.

It is a further object of the present invention to disclose the method as defined in any of the above, wherein the reporter gene allele is selected from the group consisting of Yellow Stripe allele such as ys1, ys3, Old Gold Stripe allele such as og1, Brown midrib allele such as bm1, bm2, bm3 and any combination thereof.

It is a further object of the present invention to disclose the method as defined in any of the above, wherein said reporter gene allele is designed to improve or facilitate selective detection in real time of said biosensor plant and/or a parameter associated with the biosensor plant or its environment condition.

It is a further object of the present invention to disclose the method as defined in any of the above, wherein said regulatory region comprises a promoter region, a terminator region, or a gene modulating the expression of said reporter gene.

It is a further object of the present invention to disclose the method as defined in any of the above, wherein said regulatory region comprises a transcription factor binding site, an RNA polymerase binding site, a TATA box, or a combination of structural variations thereof.

It is a further object of the present invention to disclose the method as defined in any of the above, wherein said regulatory region is responsive to a parameter or condition of said plant selected from the group consisting of physiological state of the plant, developmental state of the plant, photosynthesis status, respiration status, plant nutrition, plant hormone functions, tropisms, nastic movements, photoperiodism, water status, abiotic stress, biotic stress, environmental contamination, vegetative index, plant biomass, plant chlorophyll content, plant pigment content, presence of undesirable plants such as weeds or parasitic plants, nutrient status in the plant such as macronutrients for example nitrogen (N), phosphorus (P) and potassium (K) or derivative thereof, micronutrient or derivative thereof, secondary nutrient or element, parasitic plants such as of the *Striga* and *Orobanche* genera, water state in the plant, virus or any other plant disease or infection and any combination thereof.

It is a further object of the present invention to disclose the method as defined in any of the above, wherein said regulatory region is responsive to nitrogen deficiency in the plant.

It is a further object of the present invention to disclose the method as defined in any of the above, wherein said regulatory region is associated with the expression of GS1 (Glutamine synthetase) isoform or isoenzyme selected from Gln1-1, Gln1-2, Gln1-3, Gln1-4, Gln1-5 and Gln2.

It is a further object of the present invention to disclose the method as defined in any of the above, wherein the expression of said reporter gene phenotype is inducible by said parameter or condition of the plant or its environment or is constantly expressed in the plant.

It is a further object of the present invention to disclose the method as defined in any of the above, wherein said reporter gene has a phenotypic characteristic controlled or expressed by an endogenous or exogenous gene and/or promoter.

It is a further object of the present invention to disclose the method as defined in any of the above, wherein said endogenous or exogenous gene and/or promoter produces a product involved in the biosynthesis of a visual marker or phenotype.

It is a further object of the present invention to disclose the method as defined in any of the above, wherein said biosensor plant comprises a responsive element comprising at least one gene, at least one regulatory element or a combination thereof, responsive to a physiological condition or an environmental state or a developmental stage of the crop, said responsive element is operably linked to a visually expressed reporter gene or biomarker or phenotypic characteristic detectable by said sensor.

It is a further object of the present invention to disclose the method as defined in any of the above, wherein said biosensor plant is produced by at least one technique selected from the group consisting of breeding, genome editing, genetic modification, GMO plants, non-GMO plants, transformation by microorganisms or insects, epigenetic factors and any combination thereof.

It is a further object of the present invention to disclose the method as defined in any of the above, wherein said biosensor crop plant is produced by targeted promoter integration into the regulatory region of said reporter gene through homology-directed repair (HDR).

It is a further object of the present invention to disclose the method as defined in any of the above, wherein said biosensor plant species is *Zea mays*, said reporter gene is selected from the group consisting of Yellow Stripe allele such as ys1, ys3, Old Gold Stripe allele such as og1, Brown midrib allele such as bm1, bm2, bm3, said responsive region is Glutamine synthetase cytosolic isozyme 1 (Gln1) promoter region, and said treatment is fertilization by spot spraying.

It is a further object of the present invention to disclose the method as defined in any of the above, wherein the executed plant treatment is selected from the group consisting of: crop protection treatments, such as controlling fungus, bacteria, virus, nematode, insects, parasitic plants and weeds, herbicide application, fertilizers application, such as fertilizer composition comprising at least one nutrient including nitrogen (Nitrate. Ammonium) potassium, phosphorus or any other plant nutrient (macronutrient and/or micronutrient) or mixture of nutrients or derivatives thereof: or any other plant treatment such as irrigation (for example in drought or salt conditions), temperature control, mechanical weeding, detection of heavy metals and residual chemicals and any combination thereof.

It is a further object of the present invention to disclose the method as defined in any of the above, wherein the executed plant treatment is fertilization by spot spraying.

It is a further object of the present invention to disclose the method as defined in any of the above, wherein the biosensor plant type is selected from the group consisting of corn, soybean, wheat, cotton, rapeseed, rice, sunflower, barely, sorghum, sugar cane, potato, sugar beet, tomato, pepper, cucumber, onion, carrot, melon, watermelon, sweetcorn, *cannabis*, plant of the genus *Trifolium* such as clover or other cover crop or plant species having a creeping or spreading growth habit, fruits, open field crops, protected cultivated crops, orchid and vineyard.

It is a further object of the present invention to disclose the method as defined in any of the above, wherein said sensor is an optical, light, imaging or photon sensor, a reflectometer, a photodetector, a spectral image sensor, a smell sensor or any combination thereof.

It is a further object of the present invention to disclose the method as defined in any of the above, wherein said sensor is an imaging sensor selected from the group of consisting of RGB frequency spectrum, multispectral, hyperspectral, visible light frequency range, near infrared (NIR) frequency range, infrared (IR) frequency range, specific light wavelengths (e.g. LED and/or laser and/or halogen and/or xenon and/or fluorescent), UV frequency range and any combination thereof.

It is a further object of the present invention to disclose the method as defined in any of the above, wherein said sensor is a camera with at least one of RGB, NIR, IR or UV sensor.

It is a further object of the present invention to disclose the method as defined in any of the above, wherein said sensor is implemented with an area scan camera, a line-scan camera system or with aerial camera system.

It is a further object of the present invention to disclose the method as defined in any of the above, wherein said sensor is a reflectometer and/or photodetector.

It is a further object of the present invention to disclose the method as defined in any of the above, wherein said sensor is RGB area scan camera.

It is a further object of the present invention to disclose the method as defined in any of the above, wherein said sensor is configured for image processing using Normalized Difference Vegetation Index (NDVI) calculation for each pixel of RGB image.

It is a further object of the present invention to disclose the method as defined in any of the above, wherein said method comprises steps of identifying candidate genes with visual phenotypes to be expressed in plants, said visual phenotypes are detectable via one or more sensors and designed or customized to enable selectively detecting said biosensor crops or said parameter associated with the biosensor crop condition.

It is a further object of the present invention to disclose the method as defined in any of the above, wherein said candidate genes are configured to be operably linked to genes or regulatory region of genes sensitive to a plant parameter or condition.

It is a further object of the present invention to disclose the method as defined in any of the above, wherein said target area comprises vegetation and background area.

It is a further object of the present invention to disclose the method as defined in any of the above, wherein the area comprises desirable and undesirable vegetation.

It is a further object of the present invention to disclose the method as defined in any of the above, wherein the area is an agricultural area and the desirable vegetation is a crop.

It is a further object of the present invention to disclose the method as defined in any of the above, wherein the undesirable vegetation is a weed.

It is a further object of the present invention to disclose the method as defined in any of the above, wherein the step of sensor detecting comprises steps of (a) emitting at least one predetermined frequency wavelength from at least one light source to the target area comprising the biosensor crops, said at least one frequency wavelength is configured to detect said reporter gene phenotype; (b) detecting the reflected and/or fluorescence frequency data from said biosensor crops in the target area by a light detecting sensor; (c) processing said data to provide a signal indicative of the reporter gene expression; and (d) communicably transmitting said signal to an execution unit to exert a plant treatment responsive to the plant or a parameter associated with its condition.

It is a further object of the present invention to disclose the method as defined in any of the above, wherein said method comprises steps of emitting a combination of two wavelengths of light, preferably, invisible light and visible light.

It is a further object of the present invention to disclose the method as defined in any of the above, wherein said method comprises steps of emitting a visible red light to said target area comprising the biosensor plants and measuring reflectance and/or fluorescence, preferably fluorescence from the chlorophyll, in the near-infrared (NIR) spectrum.

It is a further object of the present invention to disclose the method as defined in any of the above, wherein said emitting step comprises emitting at least one light frequency selected from the group consisting of quasi-monochromatic light, polychromatic light, monochromatic light and combinations thereof.

It is a further object of the present invention to disclose the method as defined in any of the above, wherein said method comprises steps of emitting a frequency wavelength of 450 nm or 680 nm and measuring received light reflected from the plant due to chlorophyll excitation at 720 nm.

It is a further object of the present invention to disclose the method as defined in any of the above, wherein said light source comprises a LED light and/or laser and/or halogen and/or xenon and/or fluorescent light source.

It is a further object of the present invention to disclose the method as defined in any of the above, wherein the sensor measures reflectance and/or fluorescence of the plant.

It is a further object of the present invention to disclose the method as defined in any of the above, wherein said execution unit comprises an applicator responsive to a computational device for applying a product to the plant, such as applying herbicide, pesticide, fertilizer or other crop protection chemical or biological composition or mixtures thereof or water by real-time spot-spraying It is a further object of the present invention to disclose the method as defined in any of the above, wherein said step of detecting comprises steps of (a) acquiring image data of said target area comprising said biosensor crops, via one or more image sensors; (b) computing said image data using a computing device communicably connected to said sensor, said computing device is configured to process said data and generate an output correlated with said biosensor crop identification and/or said at least one parameter associated with the crop condition; and (c) communicating said output to a control unit configured to generate a signal communicably transmitted to an execution unit operably linked to the sensor, said execution unit is capable of applying in real time a selective treatment to said target area being responsive to said signal.

It is a further object of the present invention to disclose the method as defined in any of the above, wherein said step of computing comprises steps of computing said image data using a machine learning process.

It is a further object of the present invention to disclose the method as defined in any of the above, wherein said step of computing comprises steps of computing said image data using computer implemented algorithm trained to generate output based on the image data.

It is a further object of the present invention to disclose the method as defined in any of the above, wherein said computer implemented algorithm is trained to generate output based on predetermined feature vectors extracted from the image data.

It is a further object of the present invention to disclose the method as defined in any of the above, wherein said method comprises steps of implementing with said algorithm a training process according to a training dataset comprising a plurality of training images of a plurality of plants captured by the at least one imaging sensor, wherein each respective training image of the plurality of training images is associated with the phenotypic expression of said predefined reporter gene of at least one plant depicted in the respective training image.

It is a further object of the present invention to disclose the method as defined in any of the above, wherein said training process comprises steps of (a) capturing images of plants expressing said predefined one or more reporter genes as compared to plants absent of said predefined one or more reporter genes using an imaging sensor: (b) classifying images into classification categories by applying a tag associated with the presence or absence of said one or more visual markers; and (c) applying a computer vision algorithm to determine a set of feature vectors associated with each classification category.

It is a further object of the present invention to disclose the method as defined in any of the above, comprises steps of applying a machine learning process with the computer implemented trained algorithm to determine the presence of the predefined phenotype of said reporter gene in the imaged plant.

It is a further object of the present invention to disclose the method as defined in any of the above, wherein said algorithm is implemented with a machine learning process using a neural network with the processed data.

It is a further object of the present invention to disclose the method as defined in any of the above, wherein said machine learning process comprises computing by the at least one neural network, a tag of at least one classification category for the at least one plant, wherein the tag of at least one classification category is computed at least according to weights of the at least one neural network, wherein the at least one neural network is trained according to a training dataset comprising a plurality of training images of a plurality of plants captured by the at least one imaging sensor, wherein each respective training image of the plurality of training images is associated with said tag of at least one classification category of at least one plant depicted in the respective training image; and generating according to the tag of at least one classification category, instructions for execution by a plant treatment execution unit.

It is a further object of the present invention to disclose the method as defined in any of the above, wherein the sensor is configured for image capturing and processing, with or without using Artificial Intelligence (AI) and/or machine learning and/or neuron networks.

It is a further object of the present invention to disclose the method as defined in any of the above, wherein the sensor and/or said execution unit is operatively linked to a mobile system configured to moving along an area comprising said plants to be monitored and/or treated.

It is a further object of the present invention to disclose the method as defined in any of the above, wherein the mobile system is selected from the group consisting of a ground mobile system and an airborne mobile system.

It is a further object of the present invention to disclose the method as defined in any of the above, wherein the ground mobile system is an agricultural machinery or equipment or vehicle.

It is a further object of the present invention to disclose the method as defined in any of the above, wherein the airborne mobile system is a drone.

It is a further object of the present invention to disclose the method as defined in any of the above, wherein the mobile system is designed for applying to the target area a composition comprising at least one herbicide, pesticide, fertilizer or other crop protection chemical or biological composition or mixtures thereof.

It is a further object of the present invention to disclose the method as defined in any of the above, wherein the mobile system is designed to exert weed control over the area.

It is a further object of the present invention to disclose the method as defined in any of the above, wherein the weed control is performed by spraying herbicide or other crop protection chemical or biological composition or by mechanical weeding.

It is a further object of the present invention to disclose the method as defined in any of the above, wherein the composition is applied by real-time spot-spraying.

It is a further object of the present invention to disclose the method as defined in any of the above, wherein said step of executing a treatment comprises at least one of the following: (i) differentiation between the biosensor plant and weeds or parasitic plant, (ii) differentiation between a plant and the plant environment, (iii) identification and treatment of a pathogen, such as bacteria, virus, fungi or a parasitic plant, invasion into the plant (iv) identification and treatment of excess or deficiency of a molecule or a nutrient in the plant (v) identification and treatment of excess or deficiency of water in the plant (vi) identification and treatment of abiotic stresses such as heat, cold or salt stress, and (vii) identification and treatment of soil contaminations such as pesticide residuals, herbicide residuals, heavy metals, or radioactive materials.

It is a further object of the present invention to disclose a method for selective crop management in real time, wherein said method comprises steps of: (a) producing a biosensor crop plant comprising steps of: (i) selecting a reporter gene genomic locus, said reporter gene genomic locus comprises a gene allele having a phenotype detectable by a sensor; and (ii) modifying the regulatory region of said reporter gene allele within said genomic locus to comprise a preselected regulatory region responsive to the status of at least one parameter or condition of said biosensor crop plant or its environment, such that the expression of said reporter gene is correlated with said status of said at least one parameter or condition of said biosensor crop plant or its environment; (b) acquiring data of a target area comprising a plurality of said biosensor crop plants via said sensor and processing said data to generate a signal indicative of the expression of said phenotype of said reporter gene allele; and (c) communicating said signal to an execution unit operably linked to the sensor, said execution unit is capable of applying in real time a selective treatment to said target area comprising said biosensor plants, said treatment is being responsive to said status of said parameter or condition of the biosensor crop plant or its environment.

It is a further object of the present invention to disclose a method for producing a biosensor plant, wherein said method comprises steps of: (a) identifying at least one candidate visual marker encoding gene within a plant detectable via a sensor: (b) identifying at least one candidate gene allele responsive to the status of at least one parameter or condition of said biosensor plant or its environment; and (c) generating biosensor plants comprising said reporter gene operably linked to the regulatory region of said gene allele responsive to the status of at least one parameter or condition of said biosensor plant or its environment, via targeted genome modification technique, preferably, homology-directed repair (HDR), is indicative of at least one characteristic associated with the biosensor and detectable by a sensor system configured for detecting said one or more visual marker, said visual marker is designed for selectively detecting in real time said characteristic associated with the biosensor plant and/or at least one parameter associated with the biosensor plant condition, via said sensor.

It is a further object of the present invention to disclose a method for selective crop management in real time, wherein said method comprises steps of: (a) producing a biosensor plant as defined in any of the above; (b) growing said biosensor plant or a plurality of said biosensor plants in a target area distributed in proximity to or in mixture with a plurality of commercially valuable crop plants absent of said modified genomic locus; (c) acquiring image data of the target area comprising the plurality of said biosensor plants in proximity or in mixture with a plurality of commercially valuable crop plants absent of said modified genomic locus, via said sensor and processing said data to generate a signal indicative of the phenotypic expression of the reporter gene allele of said biosensor plant; and (d) communicating said signal to an execution unit communicably linked to the sensor, said execution unit is capable of exerting in real time a selective monitoring and/or treatment responsive to said status of said parameter or condition of the biosensor plant or its environment, to at least a portion of the target area comprising said biosensor plants in mixture with said plurality of crop plants absent of said modified genomic locus, said treatment is in direct or negative correlation with the expression of said visual marker in said biosensor plants.

It is a further object of the present invention to disclose a biosensor plant useful for selective crop management in real time, wherein said biosensor plant comprises at least one modified genetic locus comprising a predetermined visual biomarker, said visual marker is encoded by a preselected reporter gene allele having a phenotype detectable by a sensor, a regulatory region of a preselected gene allele responsive to at least one parameter or condition of said crop plant or its environment; said regulatory region is operably linked to said reporter gene, wherein the expression of said reporter gene phenotype is correlated with the status of said at least one parameter or condition of said biosensor plant or its environment.

It is a further object of the present invention to disclose the biosensor plant as defined in any of the above, wherein said phenotype comprises shape, color, leaf morphology, colorization or veins structure, plant pigment, size, viability, smell, developmental stage, physiological state, phonological stage of plant growth, stress condition, nutrient status or deprivation, chlorophyll content, plant biomass, water content or status, disease condition and any combination thereof.

It is a further object of the present invention to disclose the biosensor plant as defined in any of the above, wherein said plant is a commercial or elite variety or strain, a hybrid or an inbred line.

It is a further object of the present invention to disclose the biosensor plant as defined in any of the above, wherein said one or more visual marker is designed to improve or facilitate selective detection in real time of one or more parameters associated with the biosensor plant, its environment and or plants lacking said biosensor visual marker in proximity to said biosensor plant, condition as compared to the detection of said one or more parameters in a plant absent of said visual marker.

It is a further object of the present invention to disclose the biosensor plant as defined in any of the above, wherein said sensor system comprises an implemented computer algorithm trained to identify the expression of said visual marker and correlate it with the status of at least one parameter or condition of said biosensor crop plant or its environment.

It is a further object of the present invention to disclose the biosensor plant as defined in any of the above, wherein said visual marker is predesigned to be detectable by a sensor configured to remotely and selectively detect said visual marker in real time and provide instructions to a treatment module operably connected with the sensor to apply a treatment responsive to the biosensor plant and/or at least one parameter associated with the biosensor plant condition.

It is a further object of the present invention to disclose the biosensor plant as defined in any of the above, wherein said plant is produced by breeding, genome editing, genetic modification, GMO techniques, non-GMO techniques, epigenetics techniques or by transformation via microorganisms or insects.

It is a further object of the present invention to disclose the biosensor plant as defined in any of the above, wherein said visual marker is selected from the group consisting of expression of fluorescent proteins (FPs) such as green fluorescent protein (GFP), monomeric red and far-red FPs, reversible and irreversible photochromism in FPs. Infrared FPs (IFPs). Bacterial phytochrome (BphP)-based IFPs and Small ultra-red FP (smURFP); non-fluorescent proteins such as chromoproteins (CPs); plant pigment molecules such as anthocyanins, carotenoids, flavonoids and betalain, absorbance or reluctance property and morphology changes such as epicuticular wax (e.g. Diketone wax), trichomes. Yellow Stripe allele such as ys1, ys3, Old Gold Stripe allele such as og1, Brown midrib allele such as bm1, bm2, bm3 and any combination thereof.

It is a further object of the present invention to disclose the biosensor plant as defined in any of the above, wherein said plant expresses at least one predefined absorbance and/or reflectance and/or fluorescence or spectral property designed to be detected by at least one reflected light detecting sensor or reflectometer configured for detecting frequency reflected from the plant emitted with at least one predetermined light frequency.

It is a further object of the present invention to disclose N-biosensor plant useful for selective crop fertilization in real time, wherein said N-biosensor plant comprises at least one modified genetic locus comprising a reporter gene allele having a phenotype detectable by a sensor, said reporter gene allele is selected from the group consisting of Yellow Stripe allele such as ys1, ys3, Old Gold Stripe allele such as og1, Brown midrib allele such as bm1, bm2, bm3 and any combination thereof, a regulatory region of a gene allele responsive to nitrogen status or deficiency in the plant: said regulatory region is operably linked to said reporter gene, wherein the expression of said reporter gene phenotype is correlated with the nitrogen status in the plant.

It is a further object of the present invention to disclose seed or any plant part of the biosensor plant as defined in any of the above.

It is a further object of the present invention to disclose a sensor configured for detection of a biosensor plant as defined in any of the above.

It is a further object of the present invention to disclose a system for selective crop management in real time, wherein said system comprises: (a) at least one sensor configured for acquiring image data of a biosensor plant, said biosensor plant comprises a visual biomarker, said biomarker is encoded by a preselected reporter gene allele having a phenotype detectable by a sensor, said reporter gene is operably linked to a regulatory region of a preselected gene allele responsive to at least one parameter or condition of said plant or its environment: such that the expression of said reporter gene phenotype is indicative of the status of said at least one parameter or condition of said biosensor plant or its environment, said sensor is further configured for generating a signal indicative of the expression of said characteristic in said plant; and (b) an execution unit operably linked to the sensor, said execution unit is capable of communicably receiving said signal from said sensor and applying in real time a selective treatment to said target area comprising said biosensor plants, said treatment is being responsive to said signal and correlated with said characteristic of said biosensor plant.

It is a further object of the present invention to disclose the system as defined above, comprising an image acquisition unit comprising at least one imaging sensor configured to capture image data to detect expression of said predetermined one or more visual markers responsive to a plant or its environment condition: a controller unit comprising a processor coupled to a non-transitory memory, said processor configured to process the image data by a trained image processing algorithm to generate an output configured to be communicably transmitted for execution by an execution unit; and a plant treatment execution unit communicably receiving instructions from said controller, said execution unit is configured to providing in real-time a treatment being responsive to the plant or its environment condition.

It is a further object of the present invention to disclose a system for real-time bio-sensing and treating a predefined state of crops, the system comprising: (a) an imaging sensor configured to capture images of plants expressing predefined one or more phenotypic characteristics responsive to the state of crops; (b) a control system communicably connected to the imaging sensor comprising a processor or processors coupled to a memory, the control system configured to execute a code to cause the control system to: (i) receive image data from the imaging sensor; (ii) process the image data to classify each image according to predefined feature vectors extracted from the image data to identify said one or more phenotypic characteristics; and (iii) send instructions, based on the identified one or more phenotypic characteristics, to an execution unit operably linked to the control system to treat said predefined state of crops.

It is a further object of the present invention to disclose a computer implemented algorithm comprising code to perform the steps of the method as defined in any of the above.

It is a further object of the present invention to disclose the computer implemented algorithm as defined in any of the above, wherein the algorithm is a machine learning algorithm.

It is a further object of the present invention to disclose the computer implemented algorithm as defined in any of the above, wherein the machine learning algorithm uses verified training data.

It is a further object of the present invention to disclose an agricultural area or a crop field comprising the biosensor plant as defined in any of the above.

It is a further object of the present invention to disclose the agricultural area or crop field as defined in any of the above, wherein said agricultural area or a crop field comprises said biosensor plants as defined in any of the above, distributed in mixture with commercially valuable crop plants absent of said at least one modified genetic locus, said biosensor plants are distributed in proximity to said commercially valuable crop plants within the agricultural area or crop field.

BRIEF DESCRIPTION OF THE INVENTION

Figure 6:
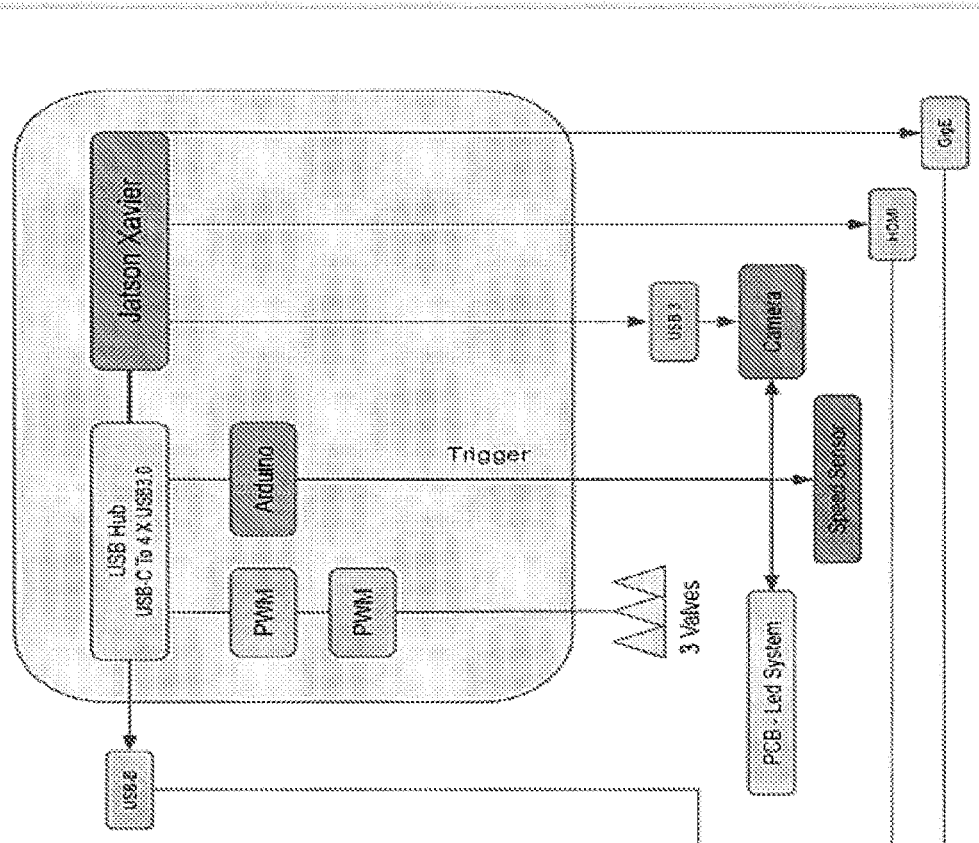
Figure 7A:
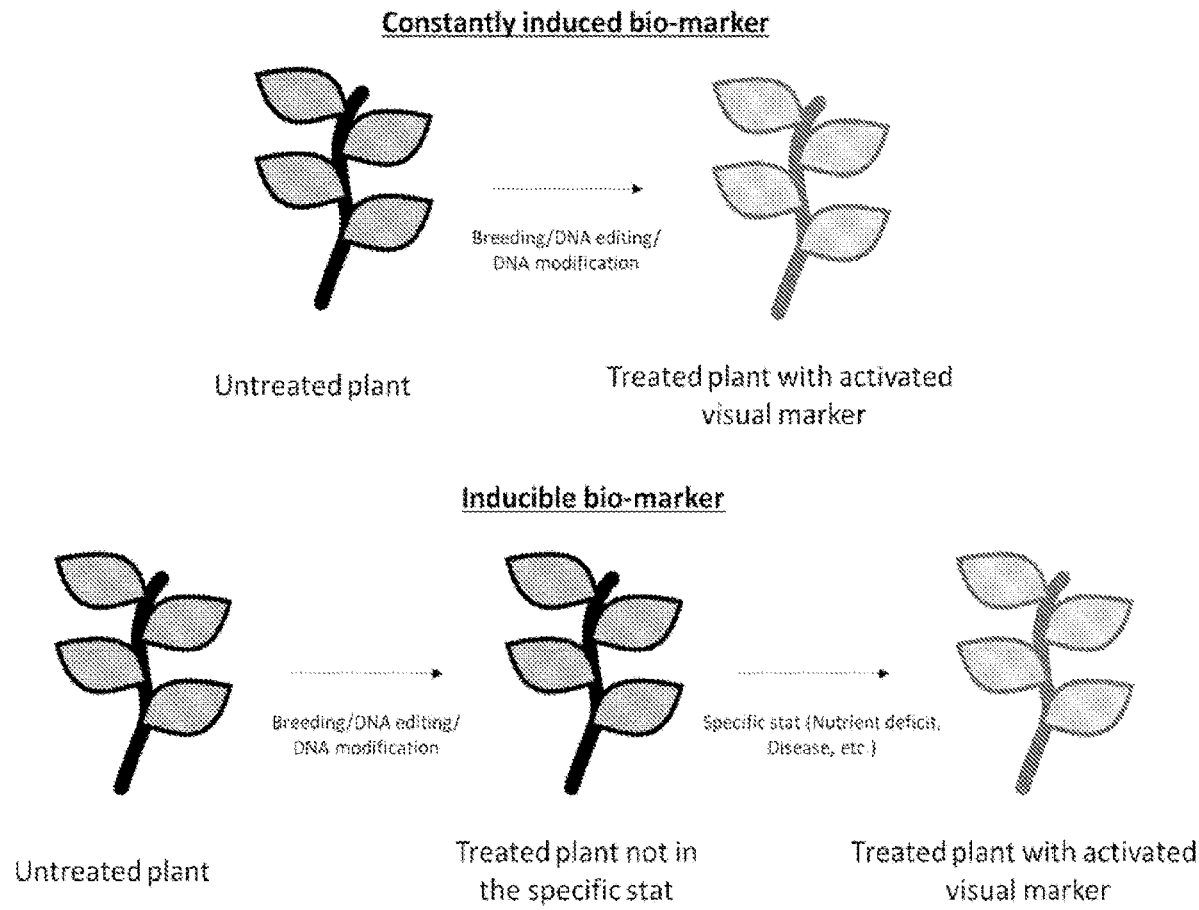
Figure 7B:
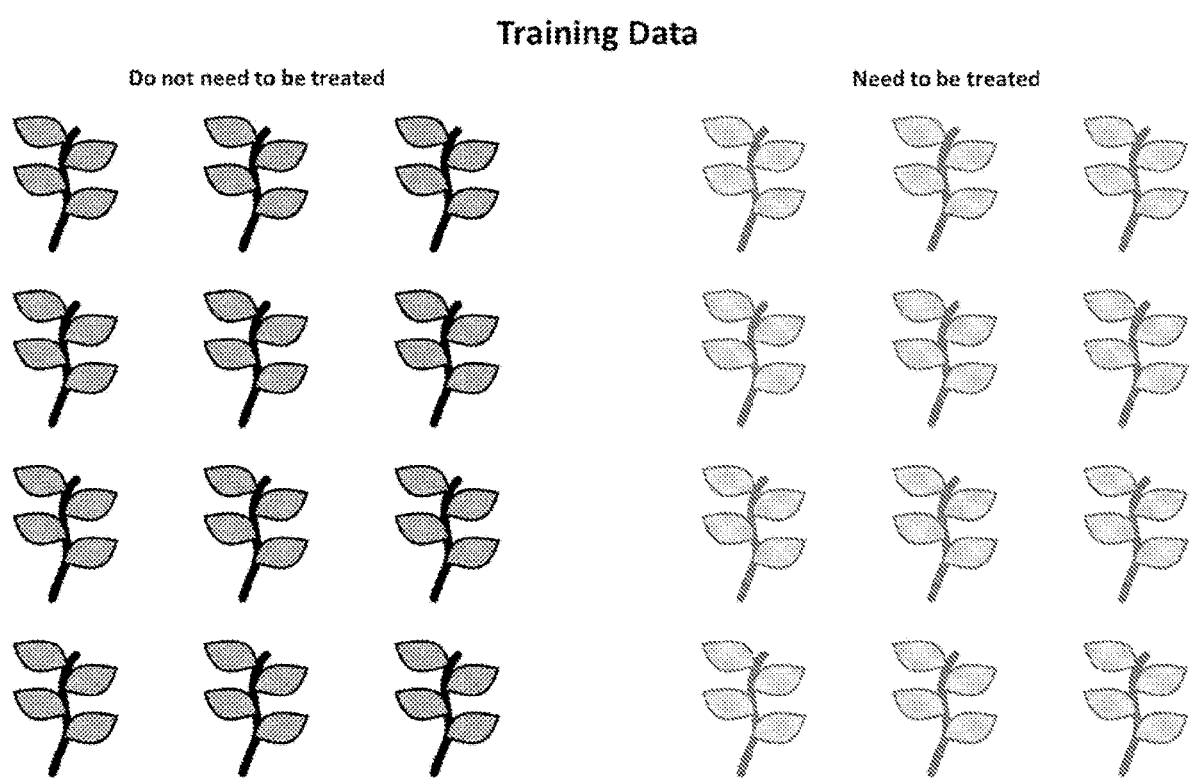
Figure 7C:
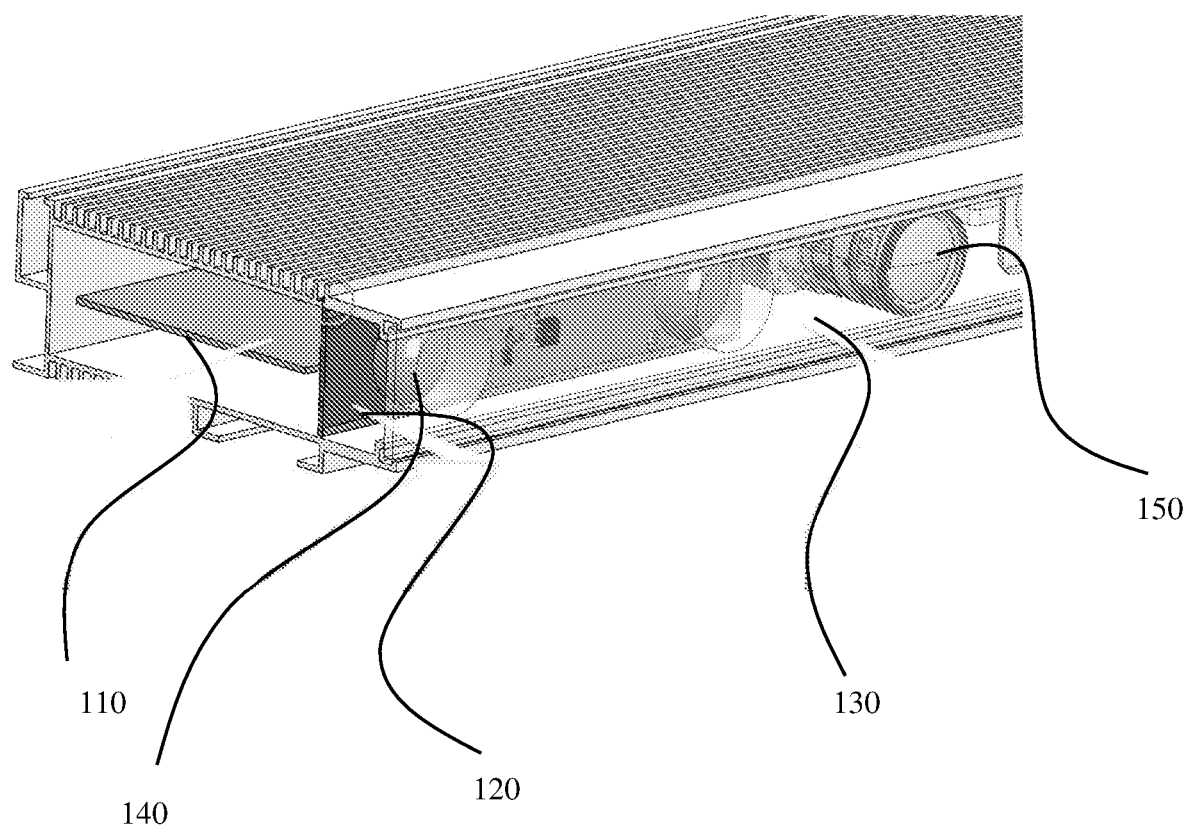
Figure 7D:
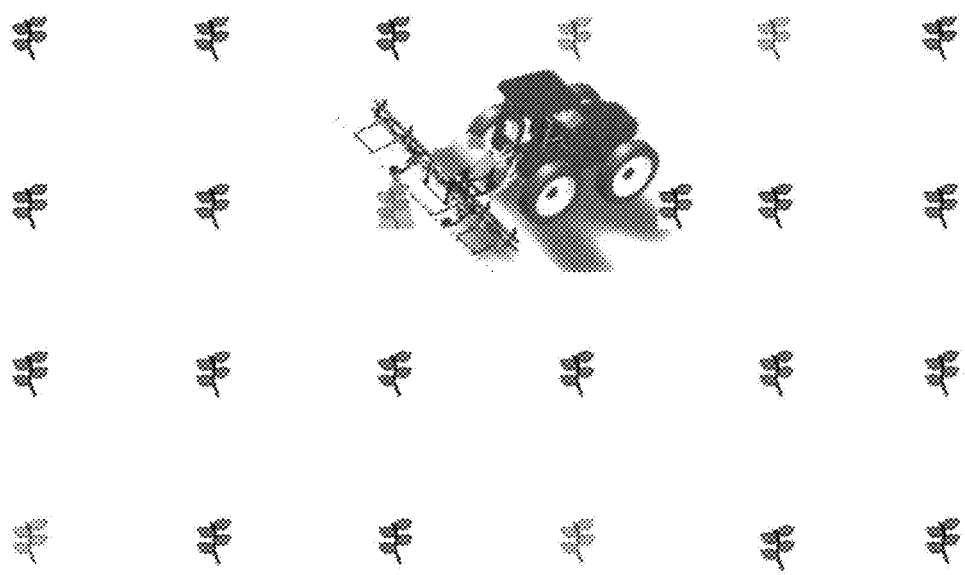

FIG. 6 is schematically presenting a block diagram of embodiments of the system for real-time plant monitoring and treatment of the present invention; and FIG. 7A-D is showing schematic illustration of alternative steps of the method of the present invention, including, production of biosensor plants expressing a phenotypic biomarker detectable by a sensor (FIG. 7A); generating a training dataset to be used to train a computer implemented algorithm for identification of the predefined phenotypic biomarker (FIG. 7B); providing at least one imaging sensor for capturing images of the target crops (FIG. 7C); and an execution unit operably connected to a mobile vehicle, e.g. an agricultural vehicle (tractor) for exerting a predefined selective treatment such as herbicide spraying, fertilization, irrigation in the area or plant in need, in real-time (FIG. 7D).

Figure 8:
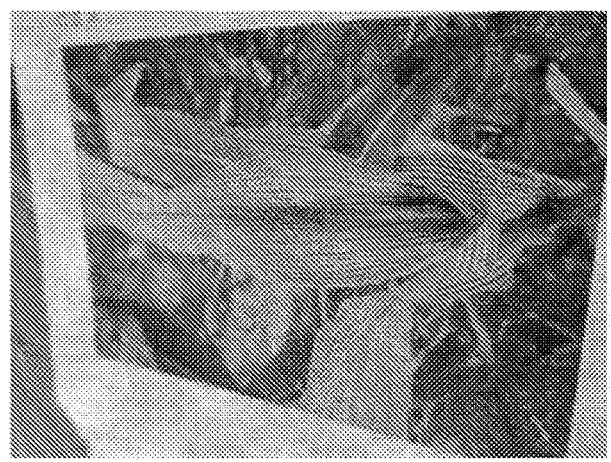
Figure 9:
Figure 10:
Figure 11:
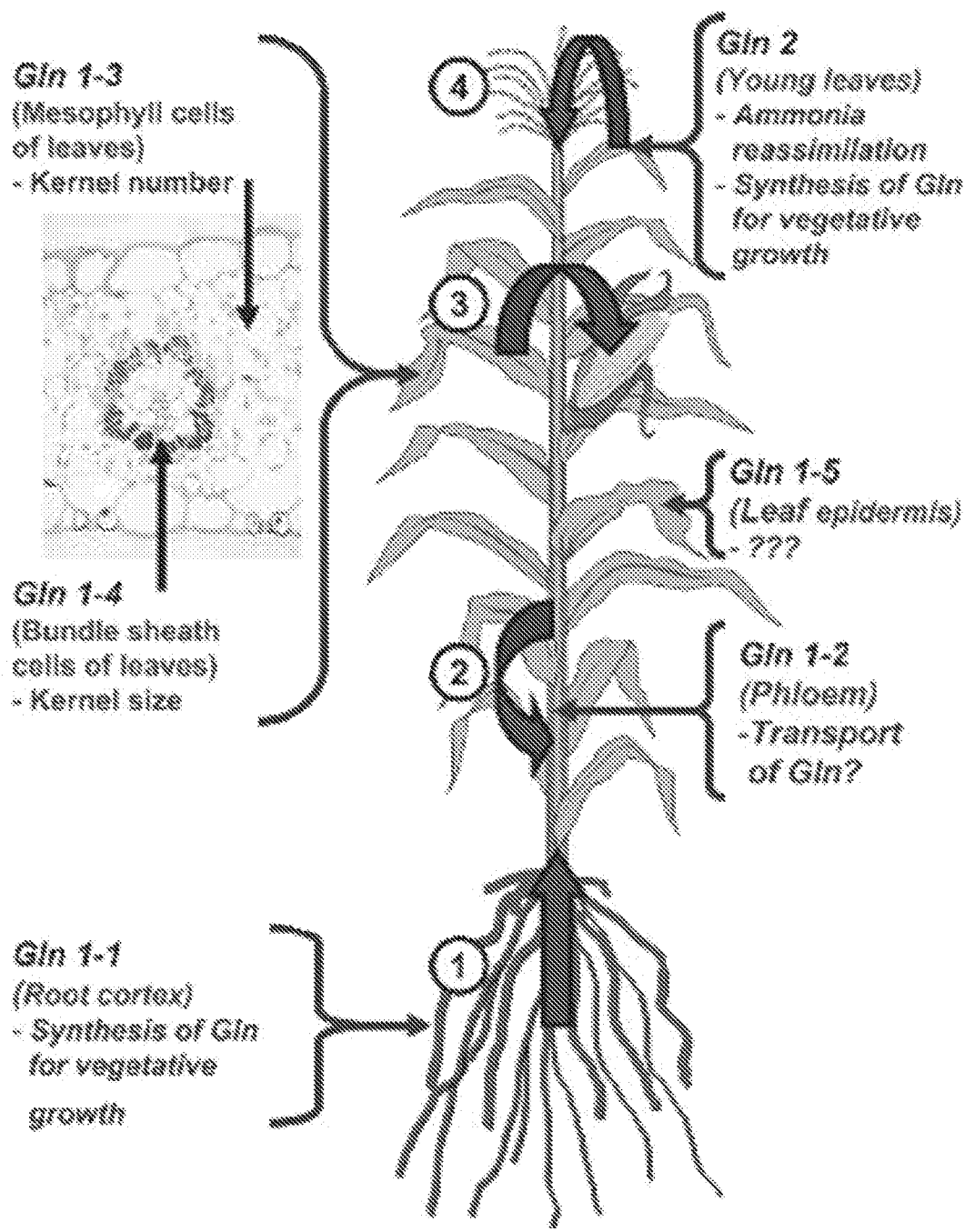
Figure 12:
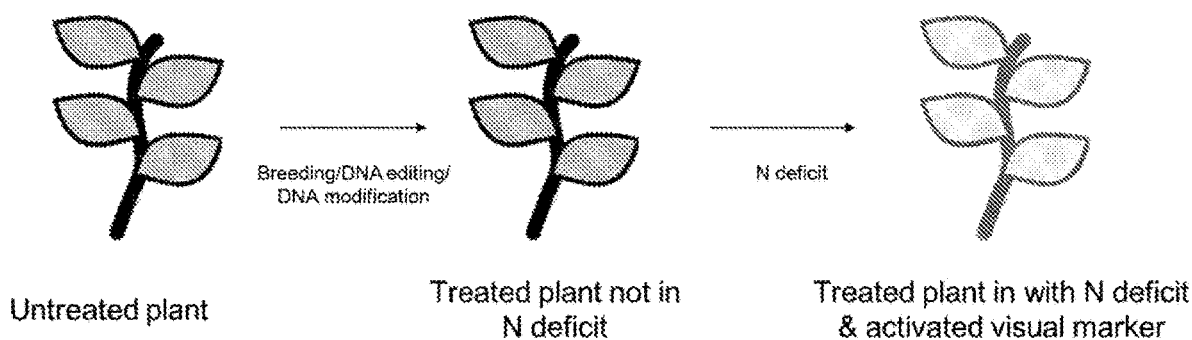
Figure 13:
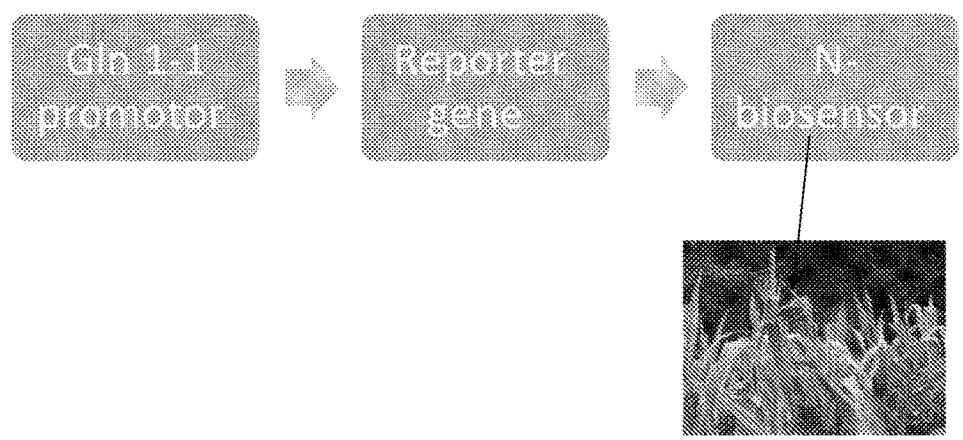
Figure 14:
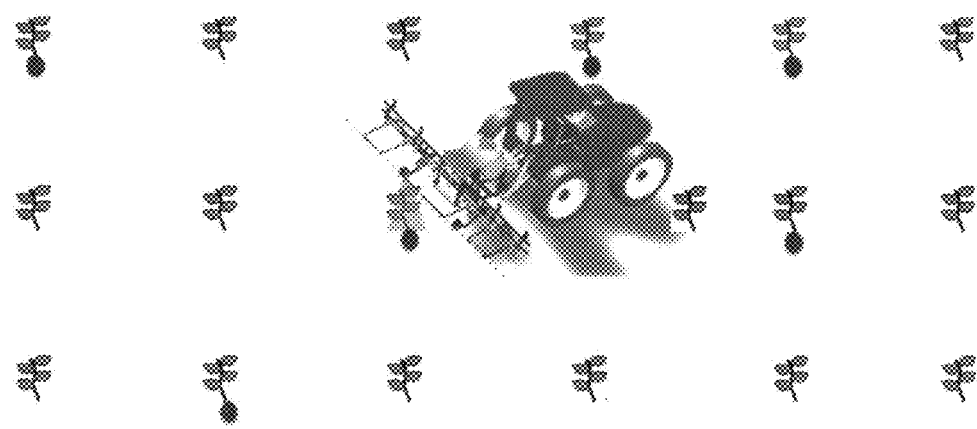

FIG. 8 is photographically presenting Yellow Stripe phenotype in ys1 and/or ys3 mutated maize plants, as embodiments of the present invention:

FIG. 9 is photographically presenting Old Gold Stripe phenotype in og1 mutated maize plants, as embodiments of the present invention:

FIG. 10 is photographically presenting Brown Midrib phenotype in bm1, bm2 and/or bm3 mutated maize plants, as embodiments of the present invention:

FIG. 11 is presenting a schematic representation depicting expression of Glutamine Synthetase (GS) isoforms, including Gln1-1, 1-2, 1-3 and 1-4 in maize plant (as published in Martin et al., Two Cytosolic Glutamine Synthetase Isoforms of Maize Are Specifically Involved in the Control of Grain Production, The Plant Cell, Vol. 18, 3252-3274, 2006, incorporated herein by reference) as optional embodiments of the present invention;

FIG. 12 is schematically describing embodiments of the method and system of the present invention for crop management in real time;

FIG. 13 is schematically presenting exemplified elements of the N-biosensor corn plants of the present invention; and FIG. 14 is schematically presenting a mixed field approach wherein the biosensor plants of the present invention are distributed in mixture with or in proximity to commercial varieties or strains or elite lines absent of a modified genomic locus expressing the visual biomarker, in a field or agricultural area or target area, as an optional embodiment of the present invention.

It will be appreciated that, for simplicity and clarity of illustration, elements shown in the figures have not necessarily been drawn accurately or to scale. For example, the dimensions of some of the elements may be exaggerated relative to other elements for clarity, or several physical

DETAILED DESCRIPTION OF THE INVENTION

In the following detailed description, numerous specific details are set forth in order to provide a thorough understanding of the disclosure. However, it will be understood by those of ordinary skill in the art that the disclosure may be practiced without these specific details. In other instances, well-known methods, procedures, components, modules, units and/or circuits have not been described in detail so as not to obscure the disclosure.

The present invention provides a method for real time selectively treating crop plants in a target area, wherein said method comprises steps of: (a) producing a biosensor crop expressing one or more predetermined visual marker, said visual marker is indicative of at least one characteristic associated with the biosensor crop and is detectable by one or more sensors configured for detecting said one or more visual marker; wherein said one or more visual marker is designed for selectively detecting in real time said characteristic associated with the biosensor crop, via said sensor; (b) acquiring data of said target area comprising said biosensor crops via said sensor and processing said data to generate a signal indicative of the expression of said characteristic associated with said crop; and (c) communicating said signal to an execution unit operably linked to the sensor, said execution unit is capable of applying in real time a selective treatment to said target area comprising said biosensor plants, said treatment is being responsive to said signal and correlated with said characteristic of the biosensor crop.

According to a further main aspect, the present invention provides a method for selective crop management in real time. The method comprises steps of:
  (a) producing a biosensor plant, said biosensor plant comprises a visual biomarker, said biomarker is encoded by at least one modified genetic locus comprising (i) preselected reporter gene allele having a phenotype detectable by a sensor, (ii) a regulatory region of a preselected gene allele responsive to at least one parameter or condition of said plant or its environment, said regulatory region is operably linked to said reporter gene, such that the expression of said reporter gene phenotype is correlated with the status of said at least one parameter or condition of said biosensor plant or its environment;
  (b) acquiring image data of a target area comprising a plurality of said biosensor plants via said sensor and processing said data to generate a signal indicative of the phenotypic expression of said reporter gene allele of said biosensor plant; and
  (c) communicating said signal to an execution unit communicably linked to the sensor, said execution unit is capable of exerting in real time a selective monitoring and/or treatment of said target area or a portion thereof comprising said biosensor plants, said treatment is being responsive to said status of said parameter or condition of the biosensor plant or its environment.

It is further within the scope of the present invention that the biosensor plant can optionally have a genetic background of a commercial or elite crop plant or line or variety or strain. Alternatively, the biosensor plant may have a genetic background of non-crop plant (i.e. absent of harvested fruits or vegetables) such as cover cop plants, for example clover or trefoil or other plant of the genus *Trifolium* or leguminous plants, grasses (including cereals) and brassicas.

In case where the biosensor plant is a commercially valuable crop plant or strain or elite line it can be seeded in a field in which all the seeds are modified to have the biosensor trait or, alternatively, it can be grown or seeded in mixture with valuable crop plants that are absent of the biosensor trait (herein referred to as mixed field approach).

In case where the biosensor plant is not crop plant such as a cover crop it is seeded in mixture with valuable crop plants that are absent of the biosensor trait (herein referred to as mixed field approach).

The mixed field approach enables to use the biosensor plants distributed within a field or agricultural area to sense or acquire data relating to important plant parameters such as water status or nitrogen status or other nutrients status on plants grown in proximity to the biosensor plant. In this way, a selective treatment in real time can be executed only to the plants or portions in the field that are in need of application of the treatment.

Thus further embodiments of the method of the present invention may include growing the biosensor plant or a plurality of the biosensor plants in a target area distributed in mixture with or in proximity to commercially valuable crop plants absent of the at least one modified genomic locus expressing the biomarker in correlation with a preselected regulatory region responsive to a parameter or condition status of the plant; acquiring the image data of said target area comprising said biosensor plants distributed in mixture with said plurality of crop plants absent of said modified genomic locus; and exerting in real time a selective treatment responsive to said status of said parameter or condition of the biosensor plant or its environment to at least a portion of the target area comprising said biosensor plants distributed in mixture with said plurality of crop plants absent of said modified genomic locus, said treatment is in direct or negative correlation with the expression of said visual marker in said biosensor plants.

According to further aspects of the present invention, the biosensor plant is a commercial or elite line, variety or strain, a cover crop plant, a hybrid or an inbred line.

It is further within the scope of the present invention to disclose the method as defined above, wherein said characteristic comprises shape, color, plant pigment, size, viability, smell, developmental stage, physiological state, phonological stage of plant growth, stress condition, nutrient status or deprivation, chlorophyll content, plant biomass, water content or status, disease condition and any combination thereof.

It is further within the scope of the present invention to disclose the method as defined in any of the above, wherein said one or more visual marker is designed to improve or facilitate selective detection in real time of said biosensor crop and/or a parameter associated with the biosensor crop condition as compared to the detection of said crop absent of said visual marker.

It is further within the scope of the present invention to disclose the method as defined in any of the above, wherein said signal is instructions for treatment positively or negatively correlated with the presence of said visual marker.

The present invention further provides a method for real time selectively treating crop plants in a target area, said method comprises steps of:

producing biosensor crops expressing one or more predetermined visual marker detectable by one or more sensors configured for detecting said one or more visual marker: said one or more visual markers are designed to enable selectively detecting in real time said biosensor crop and/or at least one parameter associated with the biosensor crop condition, via said sensor;

detecting data of said target area comprising said biosensor crops via said sensor, to generate by said sensor a signal indicative of the expression of said visual marker in said crop; and communicating said signal to an execution unit operably linked to the sensor, said execution unit is capable of applying in real time a selective treatment to said target area comprising said biosensor plants, said treatment is being responsive to said signal and correlated with said detection of said biosensor crop and/or the parameter associated with the biosensor crop condition.

According to one aspect, the system and method of the present invention is based on sensors that measure the reflectance of particular wavelengths of light, caused by the absorption and fluorescence of red light by the chlorophyll contained in green plants, i.e. the biosensor plants.

According to other aspects, the system and method of the present invention uses a combination of two wavelengths of light (invisible infrared light and visible red light), which are projected onto the target area comprising the biosensor plants, while the sensors assess the ratio difference of red and near-infrared reflectance of the vegetation and background. In one embodiment, a single source of visible red light is used and the reflectance (fluorescence) from the leaf, which occurs in the near-infrared (NIR) spectrum is measured.

According to yet another aspect of the present invention, a computer implemented method for real-time plant monitoring and treatment. The method comprises steps of:

acquiring image data of plants expressing predefined one or more phenotypic characteristics responsive to the plant or its environment condition, via at least one imaging sensor;

computing said image data using a computer implemented algorithm trained to generate output based on the image data; and communicating the generated output to a controller configured to process said output and communicably transmit instructions for execution by an execution unit operably linked to the controller, said execution unit is configured to provide in real-time a treatment being responsive to the plant or its environment condition.

In main aspects of the present invention, the visual marker or phenotypic characteristics are generated by genetic modification and/or genome editing and/or conventional breeding or epigenetic techniques. Thus the present invention is aimed at and achieves the production of plants expressing biosensor genes with phenotypic characteristic which can be easily and effectively identified by appropriate predesigned sensors. The biosensor genes are indicative of a plant status or parameter and enable selectively applying a treatment responsive to the plant status or parameter (i.e. application of an agricultural product) to the plant in need.

The present invention further provides a method for real-time monitoring and/or treatment of a plant or its environment condition, comprising steps of:

emitting at least one predetermined light frequency from a light source to a target area comprising plants expressing predefined spectral property indicative of the plant or its environment condition, said at least one frequency is configured to detect said predefined property;

detecting the reflected frequency data from said target area by a light detecting sensor;

processing via a computational device said data to provide a signal indicative of the plant or its environment condition;

communicably transmitting said signal to an execution unit to exert a plant treatment responsive to the plant or its environment condition.

It is within the scope of the present invention that the step of emitting comprises emitting visible light and/or non-visible light such as infrared or NIR light.

The invention herein disclosed is based on plants expressing biosensors and in some aspects, machine learning systems and image processing.

According to other main aspects, the present invention discloses systems and methods for real time plant monitoring and treatment by identifying a phenotypic characteristics (endogenous or exogenous) which can be expressed in plants (predetermined crops) and used as a biosensor for detecting and selectively treating the plant or a parameter associated with the plant or its environment condition. According to further aspects of the present invention, specific sensors configured to detect in real-time each of the phenotypic characteristics are designed. Such sensors may be imaging sensors communicably connected to a computer device which processes the imaging data based on machine learning algorithms. Alternatively, the sensors may be a reflectometer configured to detect reflectance from plants expressing specific absorbance/reluctance properties when irradiated with responsive wavelength frequencies.

In many cases it is very difficult to identify the exact plant state (e.g. physiological factor or condition of the plant) or to distinguish between similar species of grass and crops (for example, wheat and barley) or between similar desirable and undesirable plant species (for example wheat and weeds). In these cases usage of currently available imaging sensors would not solve the problem, as their output is based on visual features detectable by the human eye.

The present invention provides for the first time a solution to this problem and enables remote and computerized identification, monitoring and treatment of plants in real-time. The present invention offers plants expressing phenotypic change or characteristic which is detectable by suitable and specifically designed sensors to detect in real time the plant and its condition and to treat the plant as desired.

Examples of expressed phenotypic characteristic include accumulation of natural pigment molecules such as anthocyanins or carotenoids and change of absorption or emission spectrum of plant parts such as leaves (by adding a cuticular layer, a structural change of membrane proteins, etc.)

According to some embodiments, the phenotypic characteristic is produced via at least one technique including: conventional breeding, genome editing and/or genetic modification within the plant.

According to further aspects, the present invention is aimed at identifying genes and/or promotors that affect the plant's phenotype which can be detected with appropriate and predesigned sensors used for selective identification and treatment of the crop condition.

It is further within the scope of the present invention to produce and provide commercially valuable crops expressing genes or genetic modifications controlling the phenotypic characteristics responsive to the plant condition.

The invention encompasses the following aspects:

1. Phenotypic characteristics expressed by endogenous plant genes and/or promotors which are associated with the plant or its environment condition. The plants may be produced by genetic modifications and/or genome editing and/or conventional breeding techniques. The phenotypic characteristics are specifically designed to be detectable by a sensor system (such as imaging sensor) that not only is capable of identifying the plant or its environment condition but is also capable of making a decision (or real-time decision) and provide a complementary or responsive treatment selectively in real-time (as opposed to, for example, passive detection by satellite or human eye).

2. Phenotypic characteristics expressed by endogenous plant genes and/or promotors (e.g. by genetic modifications and/or genome editing and/or conventional breeding techniques) in specific developmental stages or conditions that are unexpectedly associated with specific plant physiological or environmental condition, for example early color change when the plant is sprayed against undesirable weeds or in response to low nitrogen levels.

3. Phenotypic characteristics expressed by endogenous plant genes and/or promotors (e.g. by genetic modifications and/or genome editing and/or conventional breeding techniques) designed for specific machine learning or sensing algorithms (such as RGB or a system that radiates at a specific frequency and absorbs the emission of the plant).

4. Phenotypic characteristics expressed by endogenous plant genes and/or promotors (e.g. by genetic modifications and/or genome editing and/or conventional breeding techniques) which produce specific markers that can be easily identifiable by sensors. Non limiting examples of phenotypic characteristics include plant pigments such as anthocyanins or carotenoids or wax coatings or spectral properties, namely absorbance or reflectance frequencies. Each phenotypic characteristic can be associated with a specific plant condition.

In terms of sensors—the invention provides specially trained algorithms, lightning frequency emitters and detectors, and sensors designed and configured to identify plant phenotypes aimed at improving and facilitating plant or plant status identification, and enabling selective treatment by the system of the present invention in real time.

Further embodiments of the invention include:

1. Building a dedicated or customized sensor system that is trained to identify a plant phenotype expressed as a result of endogenous (inducible or not) gene and/or promotor expression or genetic modification associated with a plant condition and preferably performs selective (real-time) plant treatment responsive to the plant condition.

2. The system is designed and trained to identify specific phenotypes that are herein disclosed, especially various visual markers such as plant natural pigments, wax coatings etc., preferably that are found to be linked with specific plants physiological conditions, or specific plant species or developmental stage important for plant growth and yield. Spot spraying (e.g. nitrogen) solutions based on normalized difference vegetative index (NDVI) values within the scope of the current invention include sensors such as Greenseeker, N-Sensor and Optrex.

The present invention provides more efficient precision spraying system and method. In some embodiments of the present invention. RGB cameras and AI algorithms are used to achieve precise and selective spot spraying of weeds and/or crop plants in crop fields such as corn fields. This desirable solution enable farmers the precision application of fertilizing compositions (such as nitrogen) in corn or any other crop.

According to one embodiment, the present invention provides a method for selective crop management in real time. The method comprises steps of: (a) producing a biosensor crop plant, said biosensor crop plant comprises a visual biomarker, said biomarker is encoded by a preselected reporter gene allele having a phenotype detectable by a sensor, said reporter gene is operably linked to a regulatory region of a preselected gene allele responsive to at least one parameter or condition of said crop plant or its environment: such that the expression of said reporter gene phenotype is indicative of the status of said at least one parameter or condition of said biosensor crop plant or its environment; (b) acquiring image data of a target area comprising a plurality of said biosensor crop plants via said sensor and processing said data to generate a signal indicative of the expression of said phenotype of said reporter gene allele; and (c) communicating said signal to an execution unit communicably linked to the sensor, said execution unit is capable of exerting in real time a selective monitoring and/or treatment of said target area or a portion thereof comprising said biosensor plants, said treatment is being responsive to said status of said parameter or condition of the biosensor crop plant or its environment.

By generating a biosensor crop plant (e.g. N-biosensor crop plant), regulation of a plant parameter (such as nutrient, e.g. nitrogen) or condition is achieved in real time. The sensing/signaling in the crop plant (such as corn) during the crop growth cycle will: (i) improve nutrient (e.g. nitrogen) fertilization requirement per unit of production, (ii) improve the grower's profitability by reducing fertilization cost and (iii) establish a sustainable solution reducing the content of chemicals in the environment and soil.

The system and method of the current invention comprises the following main features or elements:

The genetic system, comprising the herein generated biosensor seeds/plants (e.g. N-biosensor seeds/plants).

The sensing system comprising a sensor capable of detecting the biosensor plant and producing data that is processed and analyzed to provide instructions to an execution unit that exerts a treatment such as fertilizing by spot spraying.

By the unique and advantageous approach of the present invention, elite lines of different valuable crops, such as corn lines will be designed to have a unique phenotypic expression or trait (for example N-biosensor trait) that allows identification by the sensory system, preferably having AI based, machine learning capabilities.

In other words, the genetic system is capable of "sensing" the state of a parameter, such as nutrient status (e.g. nitrogen) in the plant and thus allowing the grower to operate with a responsive treatment to the plants/or area in the field in need in real time.

The biosensor trait (e.g. N-biosensor trait) has no negative effect on the crop yield quantity and quality.

According to one aspect of the present invention, the biosensor seeds/plants are used or distributed in a crop field where (1) all the plants/seeds in the field are the biosensor plants (2) the biosensor seeds/plants are used together with plants/seeds of the same crop species but absent of the biosensor feature, or (3) the biosensor seeds/plants are used together with a crop species that is different from the biosensor seeds species—for example corn biosensor seeds are sawed in proximity to other crop species, e.g. trees, in order to "sense" or report or provide information on the nitrogen status of the tree. According to other aspects of the present invention, a clover or trefoil or other plant species having a creeping or spreading growth habit is created and used as a biosensor plant within a desirable and valuable crop field enabling selective and precise fertilization of the corn plants surrounding the biosensor plants.

According to a further aspect of the present invention, at a first stage, capturing images of a crop field or agricultural area comprising the biosensor plants is performed using imaging sensors preferably linked to a mobile system configured to moving along an area. The mobile system (such as ground or airborne mobile system, e.g. drone) preferably comprises GPS and is able to perform weed control by selective spraying based on weed identification using Artificial Intelligence and machine learning technologies. At the next stage, accurate and selective fertilization (N fertilization) is applied to the agricultural area based on the imaging data of the biosensor plants derived from the expression of the visual marker which is controlled by a genetic element responsive to the status of the nitrogen in the plant.

It is further within the scope that another advantageous aspect of the current invention is that a preliminary review (scouting) of status of an agricultural area, for example nitrogen status, is performed based on the imaging data of the biosensor plants to acquire and gather fertilization important parameters such as when to fertilize and to how much fertilizer should be prepared in advance.

Although embodiments of the disclosure are not limited in this regard, discussions utilizing terms such as, for example, "processing", "computing", "communicating", "training", "capturing", "executing". "calculating", "feeding", "determining", "establishing", "analyzing", "checking", "tagging", "classifying", "transmitting", "exerting" or the like, may refer to operation(s) and/or process(es) of a computer, a computing platform, a computing system, a computer implemented algorithm or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes.

Although embodiments of the disclosure are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, use of the conjunction "or" as used herein is to be understood as inclusive (any or all of the stated options).

As used herein, the term about denotes ±25% of the defined amount or measure or value.

The term "plant" as used herein encompasses a whole plant, a grafted plant, ancestor(s) and progeny of the plants and parts thereof. The plant may be in any form including suspension cultures, embryos, meristematic regions, callus, plant cell, tissue culture, leaves, gametophytes, sporophytes, pollen, and microspores. The term "plant" encompasses a cultivar, a variety, wild type plants or genetically modified plants. It further includes desirable agricultural crops and undesirable plants such as weeds and parasitic plants.

The term "crop" or crop plant" as used herein refers to a plant or plant product that can be grown and harvested extensively for profit or subsistence. Crop may refer either to the harvested parts or to the harvest in a more refined state. Most crops are cultivated in agriculture or aquaculture. A crop may include macroscopic fungus (e.g. mushrooms), or alga (algaculture).

Most crops are harvested as food for humans or fodder for livestock. Non-food crops include horticulture, floriculture and industrial crops. Horticulture crops include plants used for other crops (e.g. fruit trees). Floriculture crops include bedding plants, houseplants, flowering garden and pot plants, cut cultivated greens, and cut flowers. Industrial crops are produced for clothing (fiber crops), biofuel (energy crops, algae fuel), or medicine (medicinal plants).

In the context of the present invention, the crop plant may be a biosensor plant or a plant absent of or lacking the biosensor trait or the modified genetic locus expressing the biosensor trait or visual marker or phenotype operably linked to a regulatory region responsive to a preselected plant parameter or condition.

The term "cover crop" or "non-crop" in agriculture refer to plants that are planted to cover the soil rather than for the purpose of being harvested. In general, cover crops manage soil erosion, soil fertility, soil quality, water, weeds, pests, diseases, biodiversity and wildlife in an agroecosystem, namely, an ecological system managed and shaped by humans. Cover crops may be an off-season crop planted after harvesting the cash crop. In the context of the present invention, the biosensor plant may be of a cover crop type. In such embodiment, the biosensor cover plant may be seeded or grown in proximity to different commercially valuable crop plants that are absent of the biosensor trait (composed of a reporter gene allele with a visual phenotype operably linked to a promoter responsive to important plant parameter such as nutrition status) and enable monitoring and/or managing important parameters such as nutrition status affecting plant development, of a commercially valuable crop line. In this way a single modified biosensor cover crop can be used for managing various species of commercially valuable or elite crop lines.

Non limiting examples of cover crop plants include, but are not limited to rye (also known as winter rye or cereal rye), Buckwheat, Clover, Sorghum, Hairy vetch, Legumes and Brassicas.

As used herein, the phrase "progeny plant" refers to any plant resulting as progeny from a vegetative or sexual reproduction from one or more parent plants or descendants thereof. For instance, a progeny plant can be obtained by cloning or selfing of a parent plant or by crossing two parental plants and include selfing as well as the F1 or F2 or still further generations. An F1 is a first-generation progeny produced from parents at least one of which is used for the first time as donor of a trait, while progeny of second generation (F2) or subsequent generations (F3, F4, and the like) are specimens produced from selfing, intercrosses, backcrosses, or other crosses of F1s, F2s, and the like. An F1 can thus be (and in some embodiments is) a hybrid resulting from a cross between two true breeding parents (i.e., parents that are true-breeding are each homozygous for a trait of interest or an allele thereof, e.g., in this case male sterile having long stigma as described herein and a restorer line), while an F2 can be (and in some embodiments is) a progeny resulting from self-pollination of the F1 hybrids.

It should be noted that the plants within the scope of the present invention encompass plants produced by any technique known in the agricultural field such as breeding, genome editing, genetic modification, GMO plants, non-GMO plants and transformation by microorganisms or insects.

The term "biosensor plant" or "biosensor crop" refers hereinafter to a plant produced by expressing in the plant a selected or predetermined visual phenotype or marker, or biomarker designed in order to enable selective detection of the plant by a sensor targeted or designed or customized for or dedicated to detecting the visual marker in the plant.

In further embodiments of the present invention, a biosensor plant comprises a visual biomarker, said biomarker is encoded by a preselected reporter gene allele having a phenotype detectable by a sensor, said reporter gene is operably linked to a regulatory region of a preselected gene allele responsive to at least one parameter or condition of said crop plant or its environment; such that the expression of said reporter gene phenotype is indicative of the status of said at least one parameter or condition of said biosensor crop plant or its environment.

According to further embodiments, a biosensor plant in the context of the present invention refers to a plant produced to have a biosensor trait comprising (1) a reporter gene allele having a visual phenotype detectable by a sensor, and (2) a regulatory region operably linked to the reporter gene encoding sequence, the regulatory region (e.g. promoter) is responsive to or controlled or regulated by the status of a plant parameter or condition such as nutrient (e.g. nitrogen) status in the plant.

According to some embodiments, the biosensor crop plant of the present invention is produced by at least one technique selected from the group consisting of breeding, genome editing, genetic modification. GMO plants, non-GMO plants, transformation by microorganisms or insects, epigenetic factors and any combination thereof.

According to further aspects of the present invention, the biosensor crop plant is produced by targeted promoter integration into and/or replacement of the regulatory region of a reporter gene through homology-directed repair (HDR). The term "selective treatment" or "selectively treating" means in the context of the present invention applying or exerting a predetermined plant treatment specifically to the plant or area (environment) in need and in a manner correlated with the plant or area or environment condition or need. Such selective treatments include: (i) differentiation between the biosensor crop and weeds or parasitic plant. (ii) differentiation between a plant and the plant environment. (iii) identification and treatment of a pathogen, such as bacteria, virus, fungi or a parasitic plant, invasion into the plant (iv) identification and treatment of excess or deficiency of a molecule or a nutrient in the plant (v) identification and treatment of excess or deficiency of water in the plant (vi) identification and treatment of abiotic stresses such as heat, cold or salt stress, and (vii) identification and treatment of soil contaminations such as pesticide residuals, herbicide residuals, heavy metals, or radioactive materials.

As used herein, the term "visual marker" or "phenotype" or "phenotypic characteristic" encompasses also the terms marker, biomarker, visual marker or visual biomarker or visual feature or visual phenotype or target feature, biosensor and reporter gene. Each of the phenotypic characteristics may form a classification category within the context of machine learning training system and method of the present invention. It refers to any observable characteristic or trait of an organism. The term covers the organism's morphology or physical form or status and structure, its developmental processes, its biochemical and physiological properties, its behavior, and its interaction with the environment. An organism's phenotype mainly results from the following factors; the expression of an organism's genetic material, or its genotype, epigenetic modifications and the influence of environmental factors. Both factors may interact, further affecting the phenotype.

A marker is any mutation or natural feature or characteristic (of a plant) that distinguishes ("marks") a strain or variety, a plant species or a plant that has specific physiological condition or developmental stage. A marker can be a gene and/or promoter mutation or replacement or element or a phenotype.

In the context of the present invention the phenotypic characteristic, marker, visual marker or visual feature, biomarker, biosensor or reporter gene is detectable by a sensor, i.e. imaging sensor and in some embodiments extractable from the image data. According to some embodiments of the present invention, the identified phenotypic characteristic is associated or linked with a physiological state of the plant and is used to biosensing and treating the plant or its environment condition. In specific aspects of the present invention a phenotypic characteristic include absorbance/reflectance property or spectral property of the plant, crop or any part thereof, when irradiated with appropriate frequencies.

Morphology is a branch of biology dealing with the study of the form and structure of organisms and their specific structural features.

This includes aspects of the outward appearance (shape, structure, colour, pattern, size), i.e. external morphology (or eidonomy), as well as the form and structure of the internal parts like bones and organs, i.e. internal morphology (or anatomy). This is in contrast to physiology, which deals primarily with function. Morphology is a branch of life science dealing with the study of gross structure of an organism or taxon and its component parts.

The term "sensor" as used herein generally refers to a device, module, machine, or system capable of detecting or measuring a property or changes in its environment and sending the information or data to other electronics, frequently a computer processor.

The term cisgenics generally encompass a sustainable approach for crop improvement. In cisgenic technology, genes from crossable plants are used and although gene introduction is used, the problem of linkage drag of other genes is overcome. The gene used in cisgenic approach is similar compared with classical breeding thus cisgenic plant should be treated equally as classically bred plant and differently from transgenic plants. It is further within the scope that cisgenics refers to genetic modification using one of the techniques of recombinant DNA technology, but no "foreign" DNA is used: in other words, the manipulation is done using DNA from the same species as the host plant, or a species that is closely related so as to be sexually compatible. According to further aspect, cisgenesis is a term describing organisms that have been engineered using a process in which genes are artificially transferred between organisms that could otherwise be conventionally bred. The genes are only transferred between closely related organisms.

The term "imaging sensor" as used herein refers to a sensor that detects and conveys information used to make an image. Without wishing to be bound by theory, an imaging sensor conveys the variable attenuation of light waves, passed through or reflect off objects, into signals, that convey the information. The waves can be light or other electromagnetic radiation. The term "image sensor" in the context of the current invention further refers to a reflectometer device. Image sensors are used in electronic imaging devices of both analog and digital types, which include digital cameras, camera modules, camera phones, and others.

Exemplary imaging sensors within the scope of the present invention include: RGB (red, green, blue), multispectral, hyperspectral, visible light frequency range, near infrared (NIR) frequency range, infrared (IR) frequency range, specific light wavelengths (e.g. LED or laser), UV frequency range, a reflectometer and combinations of the aforementioned.

The term "reflectometer" as used herein also encompass the terms light receiving sensor, light detecting sensor, light detector, reflected light receiver, photodetector and photodetector array.

It is within the scope of the present disclosure that reflectometry uses the reflection of waves at surfaces and interfaces to detect or characterize objects. There are several different forms of reflectometry. They can be classified in several ways, for example by the used radiation (electromagnetic, ultrasound, particle beams), by the geometry of wave propagation (unguided versus wave guides or cables), by the involved length scales (wavelength and penetration depth versus size of the investigated object), by the method of measurement (continuous versus pulsed, polarization resolved), and by the application domain.

The term "a parameter associated with the biosensor crop or its condition" or "a plant or its environment condition" as used herein encompass any physiological, physical, chemical, and biological characteristic, condition, status or state or interactions or combinations between more than one of the factors of the plant, its environment or interactions between them. It is noted that the system and method of the present invention enables detection in real-time of a plant or its environment condition and more than that, providing an appropriate or responsive treatment selectively to the plant or agricultural area in need in real time. The below detailed examples show specific depicted applications of the herein described system and method included within the scope of the present invention.

According to some aspects of the present invention, a plant or its environment condition may include photosynthesis, respiration, plant nutrition, plant hormone functions, tropisms, nastic movements, photoperiodism, water status, abiotic stress, biotic stress, weeds, parasitic plants, environmental contamination and any combination thereof. More particularly, a plant or its environment condition refers to nitrogen (Nitrate, Ammonium), potassium, phosphorus condition in the plant, parasitic plants such as of the *Striga* and *Orobanche* genera, chlorophyll content, presence of undesirable plants such as weeds, plant biomass, Vegetation Index, water state in the plant, virus or any other disease infection.

In the context of the present invention, the term "Vegetation Index" (VI) refers to a spectral transformation of two or more bands designed to enhance the contribution of vegetation properties and allow reliable spatial and temporal inter-comparisons of photosynthetic activity and canopy structural variations. It is further acknowledged that many of the indices make use of the inverse relationship between red and near-infrared reflectance associated with green vegetation.

Applied treatments by the system and method of the present invention include crop protection treatments, such as controlling fungus, bacteria, virus, nematode, insects, parasitic plants and weeds, herbicide application, fertilizers application, such as fertilizer composition comprising at least one plant nutrient, for example at least one macronutrient such as nitrogen (Nitrate, Ammonium), potassium and/or phosphate, at least one micronutrient or any other plant nutrient or mixture of nutrients; or any other plant treatment such as irrigation (for example in drought or salt conditions), temperature control and detection of heavy metals and residual chemicals.

It is within the scope of the present invention that the term "plant nutrient" refers hereinafter to any plant chemical element, compound or mineral or mixtures or compositions thereof necessary for plant growth, plant metabolism and proper development, including macronutrients, meso nutrient or element and micronutrients.

According to some aspects of the present invention. Macronutrient or macro elements include nitrogen (N), phosphorus (P) and potassium (K) or derivatives thereof: Meso nutrients or elements, also called secondary nutrients include magnesium (Mg), calcium (Ca) and Sulphur(S) or derivatives thereof; and Micro nutrients or elements or trace elements include iron (Fe), manganese (Mn), zinc (Zn), boron (B), copper (Cu), molybdenum (Mo) and silicon (Si) or derivatives thereof.

It is further acknowledged that in some other aspects of the invention, the term "macronutrient" generally refers to nitrogen (N), phosphorus (P), potassium (K), calcium (Ca), sulfur(S), magnesium (Mg), carbon (C), oxygen (O), hydrogen (H) and/or derivatives or combinations thereof; and the term "micronutrients" (or trace minerals) generally refers to iron (Fe), boron (B), chlorine (Cl), manganese (Mn), zinc (Zn), copper (Cu), molybdenum (Mo), nickel (Ni) and/or derivatives or combinations thereof. According to further aspects, an executed treatment responsive to the biosensing system of the present invention comprises at least one of the following: (i) differentiation between a crop and weeds or parasitic plant. (ii) differentiation between a plant and the plant environment, (iii) identification and treatment of a pathogen, such as bacteria, virus, fungi or a parasitic plant, invasion into the plant (iv) identification and treatment of excess or deficiency of a molecule or a nutrient in the plant (v) identification and treatment of excess or deficiency of water in the plant (vi) identification and treatment of abiotic stresses such as heat, cold or salt stress, and (vii) identification and treatment of soil contaminations such as pesticide residuals, herbicide residuals, heavy metals, or radioactive materials.

The term "bio-sensing system" or "plant bio-sensing system" refers to a responsive or a regulatory element comprising at least one gene and/or at least one promoter which is responsive to a condition or state of the plant or its environment. The responsive element is being operably linked or associated with the expression of a phenotypic characteristic or visual marker (might be expressed by at least one reporter gene) of the plant detectable by an image sensor.

According to some aspects of the present invention, the identified phenotypic characteristic is controlled by a gene encoding a product involved in the biosynthesis of a visual marker such as plant pigment, said gene being operably linked to a plant endogenous bio-sensing system, wherein the bio-sensing system is responsive to the plant or its environment condition.

As described above, the system of the present invention may comprise the following elements:
(a) A plant comprising a visual phenotypic characteristic or marker operably linked to a regulatory or genetic element, such as at least one gene or at least one promoter, which is responsive to a physiological condition of the plant affecting its growth and development.

(b) A remote imaging sensor system comprising an image acquiring unit and a control unit. The system is configured to capture images data of the plant and process the image data using a deep learning algorithm configured to identify the expression of predefined visual phenotypic marker in the plant image and predict a suitable treatment associated with the expressed phenotype, and An execution unit communicably connected to the imaging sensor system configured to exert a predefined selective treatment according to the prediction in real time. The treatment is being responsive to the physiological condition of the plant affecting its growth and development.

Reference is now made to Table 1 presenting exemplified plant phenotypic markers and corresponding endogenous responsive genes or associated conditions, as embodiments of the present invention.

TABLE 1

| Phenotypic biomarkers and responsive endogenous genes/promoters | | |
|---|---|---|
| Crop species | Phenotypic marker or characteristic | Responsive gene or condition |
| Triticum. spp | Diketone wax (Waxy phenotype) | TaNAC2-5A (nitrate-inducible) |
| Triticum. spp | Anthocyanin | Identification of weeds versus wheat plants |
| | three genes (Rc-A1, Rc-B1 and Rc-D1) for red coleoptile, three genes for purple culm (Pc-A1, Pc-B1, Pc-D1), three genes for purple leaf sheath (Pls-A1, Pls-B1, Pls-D1), three homoeologous for purple leaf blades (Plb-A1, Plb-B1, PlbD1), two genes for purple anther (Pan-A1 and Pan-D1) and two genes for purple pericarp, (Pp1 and Pp3) | |
| | Three homologous DFR genes of TaDFR-A, TaDFR-B and TaDFR-D localized in chromosome 3A, 3B and 3D respectively are highly expressed in red and purple wheat grains. | |
| | Five copies of ANS genes assigned to chromosomes 6A (two copies), 6B (two copies) and 6D (one copy) have been sequenced in wheat. | |
| | In purple wheat F3'5'H gene has been identified in 2AL32, F3'5'H identified in 4D chromosome of blue wheat. | |
| | Regulation of structural gene expression in the anthocyanin pathway is arranged by a ternary complex involving transcription factors from the MYB, bHLH and WD40 protein classes. | |
| | Red grain color controlled by dominant Tamyb10 genes located on the long arm of chromosomes 3A, 3B and 3D (R-A1, R-B1 and R-D1, respectively), | |
| | purple grain color by the Pp-1 genes and Pp3 located in chromosomes 7 and 2AL respectively (orthologs of both rice OsC1 and maize C1 which encode MYB-like transcription factors responsible for the activation of structural genes encrypting enzymes participating in anthocyanin biosynthesis. | |
| | Flavonoid biosynthesis pathway enzymes include: PAL: phenylalanine ammonia-lyase; CHS: Chaicone Synthase; CHI: Chaicone Isomerase; F3H: Flavanone 3-hydroxylase; F3'5'H: Flavonoid 3',5'-hydroxylase; F3H: Flavonoid 3'-hydroxylase; DFR: Dihydro Flavonol-4-Reductase; ANS: Anthocyanidin Synthase; GT: Glycosyltransferase; FS: Flavone Synthase; FLS: Flavonol Synthase; IFS: Iso Flavone Synthase; AUS: Golden Grass Synthase; ANR: Anthocyanidin reductase. | |
| Zea mays | Anthocyanin | Phosphorus or Nitrogen stress |
| Zea mays | Cytokinins | Nitrogen/Nitrate reductase |
| Zea mays | Anthocyanin | Phosphate deficiency |
| Melon | Phytoene synthase visual marker | Watermelon mosaic virus infection |
| Poaceae (monocotyledonous plants) | Fluorescence emission | UV-A radiation (e.g. N2-laser 337 nm) |

TABLE 1-continued

Phenotypic biomarkers and responsive endogenous genes/promoters

| Crop species | Phenotypic marker or characteristic | Responsive gene or condition |
| --- | --- | --- |
| Purple rice | Anthocyanins | Nitrogen |
| Tomato | Anthocyanins/Carotenoids | Parasitic plants of the *Striga* and *Orobanche* genera |
| Citrus | Visual reported gene: embryo-specific anthocyanin regulatory gene | Genetic transformation of citrus |
| *Zea mays* | Carotenoids | Phytoene synthase gene (PSY1) |
| *Zea mays* | Anthocyanin production | Maize c1, p1, a1, a4 pl genes and regulators R and C1 |
| Soybean | Fluorescent protein | Soybean disease |
| Sugar beet | Expression of butylin | Virus |
| Soybean | Carotenoids elimination | Micronutrients (e.g. copper) |
| *Zea mays* | Yellow stripe-ys1, ys3 | Promoter region of GS1 (Glutaminesynthetase) isoforms Gln1-1, Gln1-2, Gln1-3 or Gln1-4 responsive to nitrogen deficiency |
| *Zea mays* | Old Gold Stripe-og1 | Promoter region of GS1 isoforms Gln1-1, Gln1-2, Gln1-3 or Gln1-4 responsive to nitrogen deficiency |
| *Zea mays* | Brown midrib-bm1, bm2, bm3 | Promoter region of GS1 isoforms Gln1-1, Gln1-2, Gln1-3 or Gln1-4 responsive to nitrogen deficiency |

Examples of genes associated with plant phenotypic characteristic which is responsive to the plant state or physiological condition which are included with the method and system of the present invention as disclosed in Hen-Avivi, S. et al. A metabolic gene cluster in the wheat W1 and the barley Cer-cqu loci determines β-diketone biosynthesis and glaucousness. The Plant Cell 28, 1440-1460. (2016); He, X. et al. The nitrate-inducible NAC transcription factor TaNAC2-5A controls nitrate response and increases wheat yield. Plant Physiology 169, 1991-2005. (2015); Jeewani, D. C. & Hua, W. Z. Recent Advances in Anthocyanin Biosynthesis in Colored Wheat. Research Journal of Biotechnology Vol 12, 6. (2017); Takei, K., Sakakibara, H., Taniguchi, M. & Sugiyama, T. Nitrogen-dependent accumulation of cytokinins in root and the translocation to leaf: Implication of cytokinin species that induces gene expression of maize response regulator. Plant and Cell Physiology 42, 85-93. (2001); Holton, T. A. & Cornish, E. C. Genetics and biochemistry of anthocyanin biosynthesis. The Plant Cell 7, 1071. (1995); Calderon-Vazquez, C., Ibarra-Laclette, E., Caballero-Perez, J. & Herrera-Estrella, L. Transcript profiling of *Zea mays* roots reveals gene responses to phosphate deficiency at the plant- and species-specific levels. Journal of Experimental Botany 59, 2479-2497. (2008); Campbell, W. H. in Photosynthetic nitrogen assimilation and associated carbon and respiratory metabolism 35-48 (Springer, 2002).; Gowri, G., Kenis, J. D., Ingemarsson, B., Redinbaugh, M. G. & Campbell, W. H. Nitrate reductase transcript is expressed in the primary response of maize to environmental nitrate. Plant molecular biology 18, 55-64. (1992); Shaner, D. L. & Boyer, J. S. Nitrate reductase activity in maize (*Zea mays* L.) leaves: I. Regulation by nitrate flux. Plant Physiology 58, 499-504. (1976) and Konishi, M. & Yanagisawa, S. The regulatory region controlling the nitrate-responsive expression of a nitrate reductase gene, NIA1, in *Arabidopsis*. Plant and Cell Physiology 52, 824-836. (2011); Martin et al., Two Cytosolic Glutamine Synthetase Isoforms of Maize Are Specifically Involved in the Control of Grain Production. The Plant Cell. Vol. 18, 3252-3274, 2006, incorporated herein by reference).

It is within the scope of the current invention that a coding nucleic acid sequence is "operably linked" to a regulatory sequence (e.g., promoter) if the regulatory sequence is capable of exerting a regulatory effect on the coding sequence linked thereto.

As used herein, the term "promoter" refers to a region of DNA which lies upstream of the transcriptional initiation site of a gene to which RNA polymerase binds to initiate transcription of RNA. The promoter controls where (e.g., which portion of a plant) and/or when (e.g., at which stage or condition in the lifetime of an organism) the gene is expressed.

According to some embodiments of the invention, the promoter is heterologous to the isolated polynucleotide and/or to the host cell.

It is further within the context of the present invention that affecting and/or controlling or regulating gene expression can be performed also by transcription factors, post-transcriptional modifications, gene expression suppressor or activators, downstream or upstream elements.

According to some embodiments of the invention, the isolated polynucleotide is heterologous to the plant cell (e.g., the polynucleotide is derived from a different plant species when compared to the plant cell, thus the isolated polynucleotide and the plant cell are not from the same plant species).

Any suitable promoter sequence can be used by the nucleic acid construct of the present invention. Preferably the promoter is a constitutive promoter, a tissue-specific, or an inducible promoter. According to some embodiments of the invention, the promoter is a plant promoter, which is suitable for expression of an exogenous polynucleotide in a plant cell.

It is further within the scope of the present invention that target plants are produced expressing the identified phenotype or visual marker using at least one technique selected from the group consisting of breeding, genome editing, genetic modification. GMO plants, non-GMO plants and transformation by microorganisms or insects. The plants are targeted for the image acquiring process.

Genome editing is a method which uses artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Several distinct classes of nucleases have been discovered and bioengineered to date. These include the meganucleases, Zinc finger nucleases (ZFNs), transcription-activator like effector nucleases (TALENs) and CRISPR/Cas system.

It is herein acknowledged that genome editing is a powerful mean to impact target traits by modifications of the target plant genome sequence. Such modifications can result in new or modified alleles or regulatory elements.

In addition, the traces of genome-edited techniques can be used for marker assisted selection (MAS). Target plants for the mutagenesis/genome editing methods according to the invention are any plants of interest including monocot or dicot plants.

Gene editing, in the context of the present invention encompass gene knockout or gene replacement. An example of such a process may be in wheat, for example, replacement of one of the gene alleles in the biosynthesis pathway of anthocyanins by a gene or allele expressing a pigment, e.g. in a specific developmental stage, detectable by a sensor but not affecting the crop yield. In another example, a promoter of a gene responsible for expression of a plant pigment (e.g. anthocyanin) is replaced by a promoter of a gene that is sensitive to nitrogen deficiency. In such a case, the plant pigment phenotype will be expressed under nitrogen deficiency conditions. In addition, the phenotype will not be expressed after a complementary application of the appropriate nitrogen concentration to the plant.

Exemplary crop types within the scope of the present invention include, but are not limited to, corn, soybean, wheat, cotton, rapeseed, rice, sunflower, barely, sorghum, sugar cane, potato, sugar beet, tomato, pepper, cucumber, onion, carrot, melon, watermelon, sweetcorn, *cannabis*, fruits, open field crops, protected cultivated crops, orchid and vineyard.

It is further acknowledged that over expression of a polypeptide by genome editing can be achieved by: (i) replacing an endogenous sequence encoding the polypeptide of interest or a regulatory sequence under which it is placed, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-ETTR and/or 3'-ETTR, or mutations in the coding sequence).

It will be appreciated that the system described herein is capable of categorizing and exerting a selective appropriate treatment to a heterogeneous population of plants. The neural network may compute the classification category, and/or the embedding, and/or perform clustering, for remotely detecting a predefined phenotypic characteristic expressed in plants which is associated with the plant physiological condition or state. This enables efficiently identifying and monitoring crops condition in their growing area (agricultural area) in real time and selectively and automatically treating the plant(s) in need with a complementary treatment or a treatment which is responsive to their condition to enhance and improve crop yield and environmental sustainability.

According to main embodiments, the system of the present invention comprises (i) an image acquisition unit comprising at least one imaging sensor communicably linked to (i) a control unit or a controller or a computer comprising a processor, and (iii) an execution unit in-communication operably linked with the computer, configured to receive instructions from the control unit to exert a selective treatment responsive to a plant or its environment condition. In specific aspects of the present invention, the execution unit is operably linked with a vehicle moving along an area where plant monitoring and treatment is required. In one embodiment, the vehicle is a ground vehicle. In yet further embodiment, the vehicle is an agricultural ground vehicle. e.g. equipped with a sprayer. In yet another embodiment, the vehicle is an airborne vehicle.

In one embodiment, the area is an agricultural area. In the context of the invention the term "agricultural area" refers, but not limited to a land devoted to agriculture, including without limitation sown land; cropped land; permanent cropland; cultivable land; farmland; pasture; and arable land. In one embodiment the agricultural area is a field such as crop field. The agricultural area of the invention comprises desirable and undesirable vegetation. In an embodiment of the invention the desirable vegetation is a crop and the undesirable vegetation is a weed.

In the context of the invention the term "crop" refers, without limitation, to a cultivated plant that is grown on a large scale as food or feed or for biofuel production. Typical crops are grain, fruit, or vegetable. Non-limiting examples of crop types within the scope of the present invention include corn, soybean, wheat, cotton, rapeseed, rice, sunflower, barely, sorghum, sugar cane, potato, sugar beet, tomato, pepper, cucumber, onion, carrot, melon, watermelon, sweetcorn, *cannabis*, fruits, open field crops, protected cultivated crops, orchid and vineyard.

As described herein, the term "weed" refers, without limitation, to a wild plant or which is not valued where it is growing and is usually of vigorous growth and in competition with cultivated plants. In other words, a weed is a plant considered undesirable in a particular situation. "a plant in the wrong place". Examples commonly used are plants unwanted in human-controlled settings, such as farm fields, agricultural area, gardens, lawns, and parks.

According to some aspects, the image acquisition unit of the invention comprises at least one imaging sensor such as a camera, particularly an area scan camera or a line-scan camera. In one embodiment of the invention, the camera is directly attached to the vehicle. In yet further embodiment, a RGB area scan camera is directly attached to the vehicle. In one embodiment, a line scan camera is TDI line scan camera. In another embodiment, the line scan camera of the invention comprises normal lens, wide angle lens, ultrawide angle lens, and fish eye lens.

In a main embodiment of the invention, image data is acquired by the image acquisition unit.

In the context of the present invention the term "computer" stands for but no limited to a machine or device that performs processes, calculations and operations based on instructions provided by a software or hardware program. The term computer also means in the context of the present invention a control unit or controller. It is designed to process and execute applications and provides a variety of solutions by combining integrated hardware and software components. The computer of the invention is configured to extract a predetermined set of feature vectors from the image data; to compute plant phenotypic characteristics based on the set of feature vectors; to generate plant treatment output and to transmit the output to the plant treatment execution unit. The plant treatment output of the invention refers, but not limited to any type of instructions in any form as to the type of treatment to be selectively applied (or not applied) in real-time to the plant or its environment. e.g. an agricultural area. The execution unit comprises means for exerting the plant treatment over the plant or area determined by the computer to be in need of the specific treatment. In the context of the invention, means for exerting the treatment stand for any system or device configured to apply such a treatment (application of herbicide, pesticide, fertilizer, irrigation etc.) in any form to the plant or area in need.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages. The computer readable program instructions may execute entirely on the user's computer, partly on the user's computer, as a stand-alone software package, partly on the user's computer and partly on a remote computer or entirely on the remote computer or server. The remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

According to certain aspects, the method of the present invention comprises steps of applying a machine learning process with the computer implemented trained algorithm to determine the presence of the predefined phenotypic characteristic in the imaged plant. Thus it is within the scope of the present invention that the algorithm (or computer readable program) is implemented with a machine learning process using a neural network with the processed data.

The term training in the context of machine learning implemented within the system of the present invention refers to the process of creating a machine learning algorithm. Training involves the use of a deep-learning framework and training dataset. A source of training data can be used to train machine learning models for a variety of use cases, from failure detection to consumer intelligence.

Inference: Inference refers to the process of using a trained machine learning algorithm to make a prediction. A trained machine learning model, enabling predictions that can guide decision logic on the device.

The neural network may compute a classification category, and/or the embedding, and/or perform clustering, for identifying a predefined expressed phenotype associated with the plant condition, i.e. physiological state to enable selective treatment of the plant in real time.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks herein disclosed.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term "classifying" may sometimes be interchanged with the term clustering or tagging, for example, when multiple plant images are analyzed, each image may be classified according to its predefined feature vectors and used to creating clusters, and/or the plant images may be embedded and the embeddings may be clustered. The term classification category may sometimes be interchanged with the term embedding, for example, the output of the trained neural network in response to an image of a plant may be one or more classification categories, or a vector storing a computed embedding. It is noted that the classification category and the embedding may be outputted by the same trained neural network, for example, the classification category is outputted by the last layer of the neural network, and the embedding is outputted by a hidden embedding layer of the neural network.

The architecture of the neural network(s) may be implemented, for example, as convolutional, pooling, nonlinearity, locally-connected, fully-connected layers, and/or combinations of the aforementioned.

An exemplary method of training the neural network(s) is described with reference to FIG. 3. FIG. 6 and FIG. 7.

It is noted that the tagging and classifying of the plants in the images or the phenotypic characteristic targets may be manually or semi manually entered by a user (e.g., via the GUI, for example, selected from a list of available phenotypic characteristics targets), obtained as predefined values stored in a data storage device, and/or automatically computed.

In an embodiment where no target feature or marker is provided, the plants are clustered according to embeddings computed by the embedding layer of the neural network. The clusters include plants most similar to one another. Clusters are created according to training of the algorithm to identify plants according to defined category or tag, for example, crop plant (e.g. cereal crop plant such as wheat) versus weed, or identification of specific plant species.

The term "feature vector" refers hereinafter in the context of machine learning to an individual measurable property or characteristic of a phenomenon being observed e.g., detected by a sensor. It is herein apparent that choosing an informative, discriminating and independent feature is a crucial step for effective algorithms in pattern recognition, machine learning, classification and regression. Features are usually numeric. A set of numeric features can be conveniently described by a feature vector. Algorithms using classification from a feature vector include nearest neighbor classification, neural networks, and statistical techniques.

In pattern recognition and machine learning, a feature vector is an n-dimensional vector of numerical features that represent an object. Many algorithms in machine learning require a numerical representation of objects, since such representations facilitate processing and statistical analysis. When representing images, the feature values might correspond to the pixels of an image.

In computer vision and image processing, a feature is an information which is relevant for solving the computational task related to a certain application. Features may be specific structures in the image such as points, edges or objects. Features may also be the result of a general neighborhood operation or feature detection applied to the image. When features are defined in terms of local neighborhood operations applied to an image, a procedure commonly referred to as feature extraction is executed.

In the context of the present invention, the computer implemented algorithm is trained to generate output based on predetermined feature vectors extracted from the image data of the plants to be monitored and/or treated using the system and method of the present invention.

One or more images of the plants may be captured, for example, each image may be captured using a different imaging sensor, and/or at a different frequency. In another implementation, the image includes multiple channels, corresponding to different frequencies.

According to further aspects of the invention, a single image may include multiple plants, or a single image may include a single plant.

It is further within the scope of the current invention that the neural network computes the classification category at least according to weights and/or architecture of the trained neural network. In some implementations, explicitly defined features (e.g., based on visual and/or physical properties of the plant, such as plant pigment, size, shape, texture) may be extracted and analyzed in addition to the features automatically extracted according to weights of the trained neural network. While, non-neural network statistical classifiers, at least extract explicitly defined features indicative of visual and/or physical properties of the plants, the trained neural network(s) does not necessarily extract such explicitly defined features. Although the neural network may implicitly learn such features during training, but unlike training for non-neural network statistical classifiers such visual and/or physical features are not explicitly defined for the neural network.

The tagging or indication of the classification categories outputted by the trained neural network(s) may be an absolute classification category, and/or a probability of falling into the classification category.

The neural network(s) may compute an embedding for the plant image. The embedding may be stored as a vector of a predefined length. The embedding may be outputted by an embedding layer of the neural network, which may be the same neural network trained to output the classification category. The embedding layer may be an intermediate and/or hidden layer of the neural network trained to output the classification category. Layers after the embedding layer may be removed from the neural network, such that the embedded values are outputted by the embedding layer acting as the final layer.

Optionally, the classification category is determined according to an annotation of an identified embedded image that is similar to the embedding computed for the target plant image being analyzed. The embedded image may be obtained from the training dataset storing embeddings of the training images computed by the embedding layer of the trained neural network. The similar embedded image may be identified according to a requirement of a similarity distance between the embedding of the target image and the embedding of the training image. The similarity distance may be computed as a distance between a vector storing the embedding of the target image and each vectors each storing embedding of respective training images. Alternatively, the similarity distance is computed between the embedding of the target image and a cluster of embeddings of training images each associated with the same classification category or tag. The distance may be computed to the center of the cluster, and/or edge of the cluster.

According to one embodiment, when multiple images are received, each of a single plant of a respective classification category. i.e. phenotypic characteristic. Clusters may be created according to the images, where images classified into the same classification category are in the same cluster. Alternatively or additionally, the images of the plants are clustered according to the embeddings computed for each plant image.

The plants may be selectively treated according to the created clusters by the execution unit according to generated instructions for treating the plants corresponding to the clusters (e.g., herbicide spraying, pesticide application, fertilization with an appropriate fertilizer nutrient composition).

As used herein, the term "hyperspectral" or "hyperspectral imaging" or "HIS" refers herein after to a spectral imaging technique which collects and processes information from across the electromagnetic spectrum. The goal of hyperspectral imaging is to obtain the spectrum for each pixel in the image of a scene, with the purpose of finding or detecting objects or features, identifying materials, or detecting processes. In general there are two branches of spectral imagers. There are push broom scanners and the related whisk broom scanners, which read images over time, and snapshot hyperspectral imaging, which uses a staring array to generate an image in an instant. In other words, hyperspectral imaging, or imaging spectroscopy, combines the power of digital imaging and spectroscopy. For each pixel in an image, a hyperspectral camera acquires the light intensity (radiance) for a large number (typically a few tens to several hundred) of contiguous spectral bands. Every pixel in the image thus contains a continuous spectrum (in radiance or reflectance) and can be used to characterize the objects in the scene with great precision and detail.

It is further within the scope of the present invention that in hyperspectral imaging, the recorded spectra have fine wavelength resolution and cover a wide range of wavelengths. Hyperspectral imaging measures continuous spectral bands.

It is acknowledged that hyperspectral deals with imaging narrow spectral bands over a continuous spectral range, producing the spectra of all pixels in the scene. For example, a sensor with only 20 bands can also be hyperspectral when it covers the range from 500 to 700 nm with 20 bands each 10 nm wide.

NIR hyperspectral imaging (NHI) is another NIR technology for chemical characterization and has been shown to be a useful tool in the characterization of biological materials. The image has spatial coordinates in two dimensions as well as a wavelength coordinate, yielding a three-dimensional hypercube. According to further embodiments. NIR hyperspectral imaging provides NIR spectral data as a set of images, each representing a narrow wavelength range or spectral band. The advantage compared to NIR spectroscopy is that, due to the additional spatial dimension provided by this technology, the images can be analyzed and visualized as chemical images providing identification as well as localization of chemical compounds in non-homogenous samples.

It is further acknowledged that hyperspectral imaging is a chemical imaging technique based on reflectance spectroscopy (the light reflected by materials). Such a device makes the collection of reflectance spectra in each point of the field of view for the Near Infrared range (it may be complementary to another device for the visible range). The hyperspectral image cube obtained can be considered both as a stack of wavelength-resolved images and as a series of spectra.

It is noted that the term "multispectral" generally refers to an image produced by sensors that measure reflected energy within several specific sections (also called bands) of the electromagnetic spectrum. Multispectral sensors usually have between 3 and 10 different band measurements in each pixel of the images they produce. It may be obtained using a remote sensing radiometer. Hyperspectral sensors measure energy in narrower and more numerous bands than multispectral sensors. Hyperspectral images can contain as many as 200 (or more) contiguous spectral bands. The numerous narrow bands of hyperspectral sensors provide a continuous spectral measurement across the entire electromagnetic spectrum and therefore are more sensitive to subtle variations in reflected energy. Images produced from hyperspectral sensors contain much more data than images from multispectral sensors. In general, it derives from an imaging spectrometer.

It is further within the scope of the current invention that in the field of hyperspectral imaging, several image acquisition methods exist, including spectrum scanning techniques, snapshot image acquisition, spatial scanning image acquisition, and spectral-spatial scanning image acquisition. It is acknowledged that hyperspectral imaging devices produce a substantial amount of 'raw' or unprocessed data. In order to make this data relevant in a horticultural or other commercial context, the raw data must be processed to generate an analysis frame, which can then be further analyzed by computer vision algorithms also referred to as configurable application to generate quantifiable data (output or analysis results).

In one embodiment provided herein, the camera includes a hyperspectral camera exhibiting several channels, each having a unique spectral response. In an embodiment of the invention, the camera exhibits a response in the range of 400-1000 nm. In other embodiments, the camera can include a hyperspectral camera exhibiting a response in the range of and 900-1700 nm. It is emphasized that the spectral response may include any number of values throughout the range. For example, for a range of 400-900 it may reflect a value for every range point (e.g. value for 400 nm. 401 nm. 402 nm, etc. up to 900 nm). According to other aspects, the spectral response includes only partial values (e.g. X values) within the range (for example, values of 480, 517, 690, 730, 850-only 5 value points).

In the context of the present invention, hyperspectral sensors and processing systems are used for detecting visual markers phenotypically expressed in plants and used as biosensors by their linkage or association with a predefined physiological state of the plant or its environment.

It is further within the scope of the present invention to use hyperspectral remote sensing, for example by wireless network, wireless network interface card (NIC) or Bluetooth.

According to further embodiments of the present invention, the system and method of the present invention combines the usage of hyperspectral imaging and near infrared (NIR) spectrometry or reflectance.

Embodiments of the present invention further provide a connected system for providing lighting, comprising one or more lighting devices, for example, an RGB camera, a stereoscopic camera, a hyperspectral camera, a near infrared camera or device.

Embodiments of the present invention can further provide a method of bio-sensing a plant condition or physiological state linked to a visually detectable phenotypic characteristic of the plant, comprising acquiring, via one or more cameras or imaging sensors, one or more image frames of a plurality of plants, preferably expressing a predefined phenotypic characteristic associated with the plant condition or physiological state; transmitting the one or more image frames to a processor trained to identify the predefined phenotypic characteristic; generating, via the processor, one or more output results representing at least one of plant condition or physiological state results; storing the one or more output results and image frames in a database and sending instructions to an execution unit to execute a treatment responsive to the identified plant condition or physiological state.

According to some embodiments, the computer vision algorithm(s) or configurable application is cloud based.

According to some embodiments, the received output for each captured image is based on image analysis results and on reflection analysis results of the plant.

In various embodiments, image processing algorithms also referred to as a configurable applications are utilized to process at least one image having at least one spectral response channel, producing analysis results representing plant physiological condition or plant characteristics.

The imaging sensor may be a device that emits light onto a plant or its environment and receives or senses (e.g., using a built-in sensor) light reflected from the object.

According to further embodiments, the present invention discloses the computer implemented algorithm or configurable application as defined in any of the above, wherein the processing unit uses a machine learning algorithm.

According to one embodiment, optional phenotypic characteristics or visual markers used in the system and method of the present invention include, but are not limiting to, fluorescent proteins (FPs) such as green fluorescent protein (GFP), monomeric red and far-red FPs, reversible and irreversible photochromism in FPs, Infrared FPs (IFPs), Bacterial phytochrome (BphP)-based IFPs and Small ultrared FP (smURFP); non-fluorescent proteins such as chromoproteins (CPs); pigment molecules such as anthocyanins, carotenoids such as carotene and lutein, flavonoids including anthocyanins and anthoxanthins, and alkaloids including betalain, papaverine and berberine and morphology changes such as hair, cuticle etc. for example expressed as epicuticular wax (e.g. Diketone wax), trichome, Yellow Stripe allele such as ys1, ys3, Old Gold Stripe allele such as og1, Brown midrib allele such as bm1, bm2, bm3 and any combination thereof.

According to a further embodiment, non-limiting examples of crop types within the scope of the present invention include corn, soybean, wheat, cotton, rapeseed, rice, sunflower, barely, sorghum, sugar cane, potato, sugar beet, tomato, pepper, cucumber, onion, carrot, melon, watermelon, sweetcorn, *cannabis*, fruits, open field crops, protected cultivated crops, orchid, vineyard, plant of the genus *Trifolium* such as clover or other cover crop or plant species having a creeping or spreading growth habit.

According to a further embodiment, non-limiting examples of plant treatment types within the scope of the present invention include crop protection treatments, such as controlling fungus, bacteria, virus, nematode, insects and weeds: fertilizers, such as fertilizer composition comprising at least one of nitrogen (Nitrate, Ammonium), potassium, phosphate or any other plant nutrient or mixture of nutrients; or any other plant treatment such as irrigation (for example in drought or salt conditions), temperature control and detection of heavy metals and residual chemicals.

Figure 1:
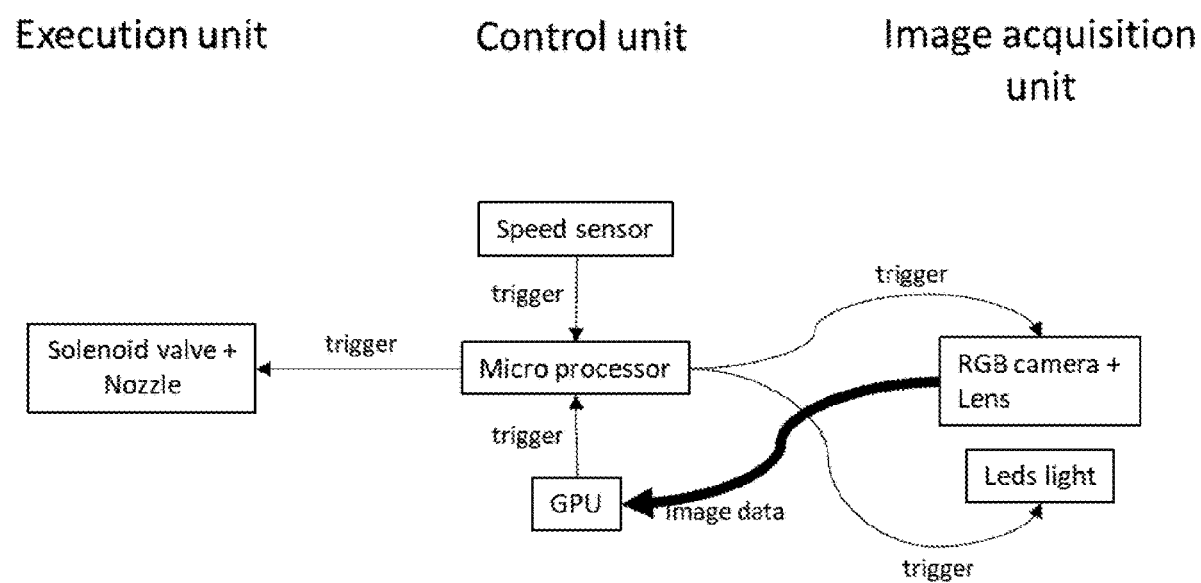
FIG. 1 is a high-level block diagram depicting a configuration of embodiments of the system for real time plant monitoring and treatment, in accordance with some embodiments of the present disclosure.

Reference is now made to FIG. 1 illustrating a high-level block diagram of exemplary embodiments of the system for real-time monitoring and treatment of plants disclosed inter alia. The system comprises an image accusation unit 100 comprising at least one imaging sensor (such as RGB camera) suitable for capturing images of plants expressing predetermined biosensors. For example, an RGB imaging sensor can use sun light or artificial light such as led light, as a source of light. The imaging data produced by the image accusation unit 100 is received by a control unit 200 comprising a computing device. In some embodiments the control unit comprises a speed sensor module, a microprocessor module and a GPU module. The control unit 200 is in communication with both the image accusation unit 100 and with an execution unit 300. It is within the scope of the present invention that the control unit is designed for speed measurement, image trigger through image acquisition 100, image processing and treatment trigger using execution unit 300. In some specific embodiments of the present invention the exaction unit 300 comprises at least one electric or solenoid valve that control one or more nozzles designed for providing a treatment such as an herbicide, a fertilizer or a pesticide.

Figure 2:
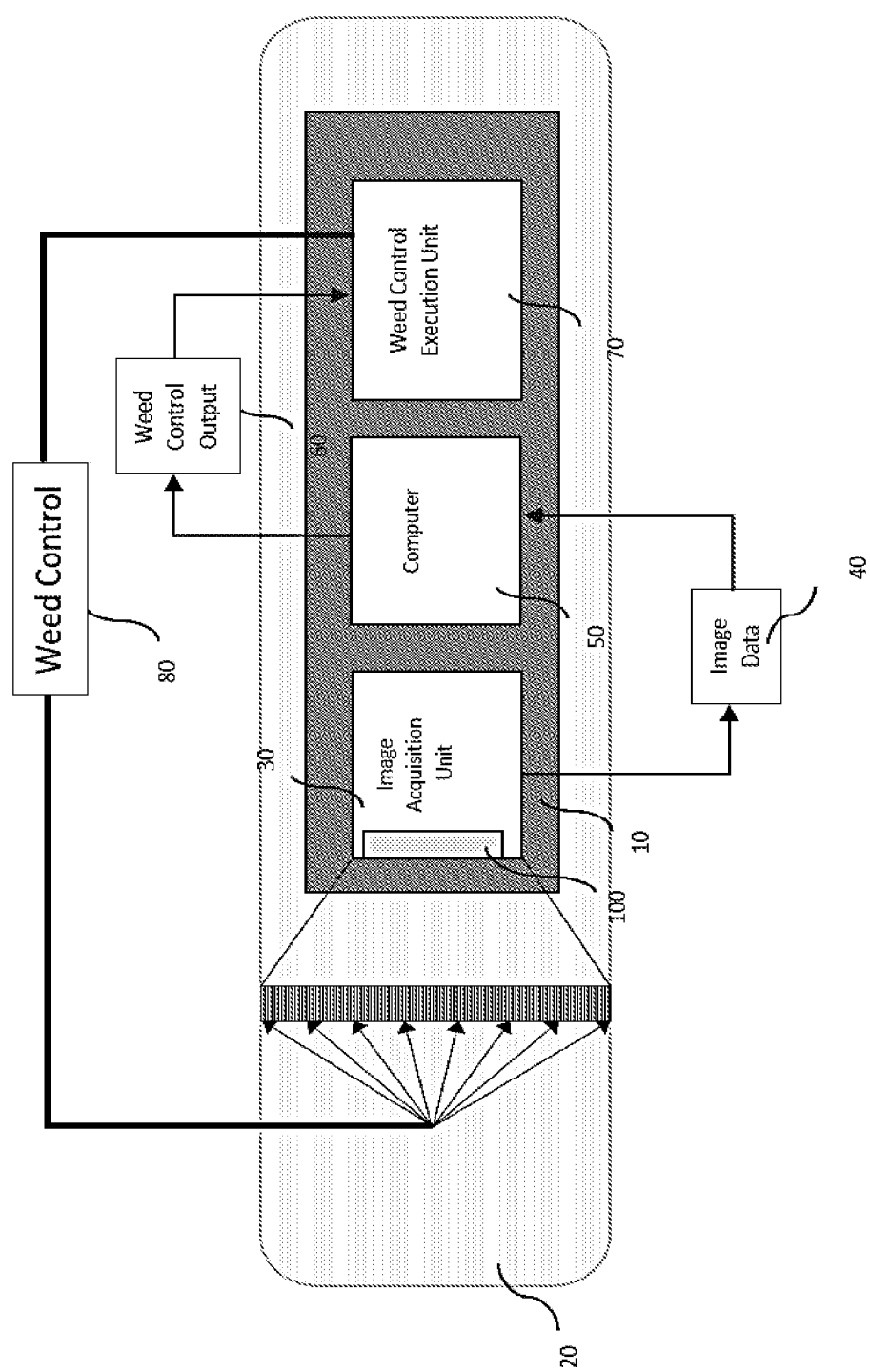
FIG. 2 is a high-level block diagram of an exemplary embodiment describing a real-time autonomous weed control system, in accordance with some embodiments of the present disclosure.

Reference is now made to FIG. 2 illustrating a high-level block diagram of an exemplary embodiment of a real-time autonomous weed control system comprising a vehicle 10, an image acquisition unit 30 operatively attached to the vehicle 10, a computer 50 responsive to the image acquisition unit 30, and a weed control execution unit 70 in-communication with the computer 50 operatively linked to the vehicle 10. The vehicle 10 is moving along an area where weed control is required 20. In one embodiment, the vehicle 10 is a ground vehicle. In yet further embodiment, the vehicle 10 is an agricultural ground sprayer. In yet another embodiment, the vehicle 10 is an airborne vehicle.

Figure 3:
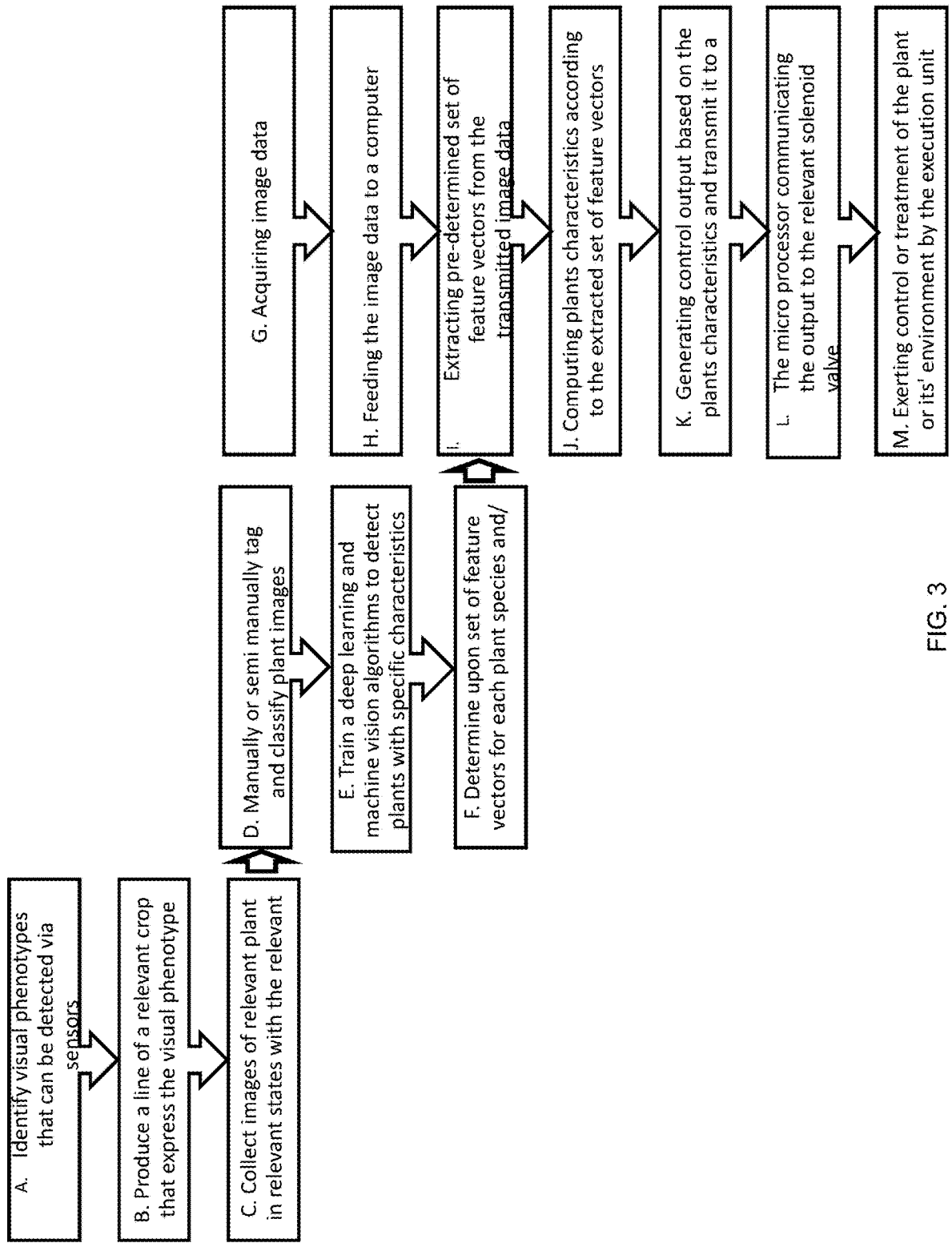
FIG. 3 is a flow diagram depicting steps for performing a the method for real time monitoring and treatment of plants, in accordance with some embodiments of the present disclosure.

FIG. 3 illustrates a high-level flowchart of exemplary embodiments of the method of the present invention, comprising steps of:
A. Identifying visual phenotypes that can be detected via relevant sensors;
B. Using breeding and/or genome editing and/or genetic modifications to generate a line of a relevant crop that express the visual phenotype in a relevant plant state or condition;
C. Growing the new line of plants and collect images of the plant in the relevant state or condition with the relevant sensor;
D. Manually or semi manually tagging and classifying the plants in the images;
E. Training a deep learning and machine vision algorithms to detect plants and differentiate between relevant species and/or states or conditions, e.g. physiological conditions;
F. Determining upon a set of feature vectors for each plant species and/or state or condition;
G. Acquiring image data of plants expressing the identified phenotype of step A;

H. Feeding the image data to a computer or computing device;
I. Extracting pre-determined set of feature vectors from the transmitted images of step H;
J. Computing plants characteristics according to the extracted set of features;
K. Generating control output based on the plants characteristics and transmit it to a micro processor;
L. The micro processor communicates the output to the execution unit, i.e. relevant solenoid valve; and
M. Exerting control over the plant/area in need of control or treatment by the execution unit.

Figure 4:
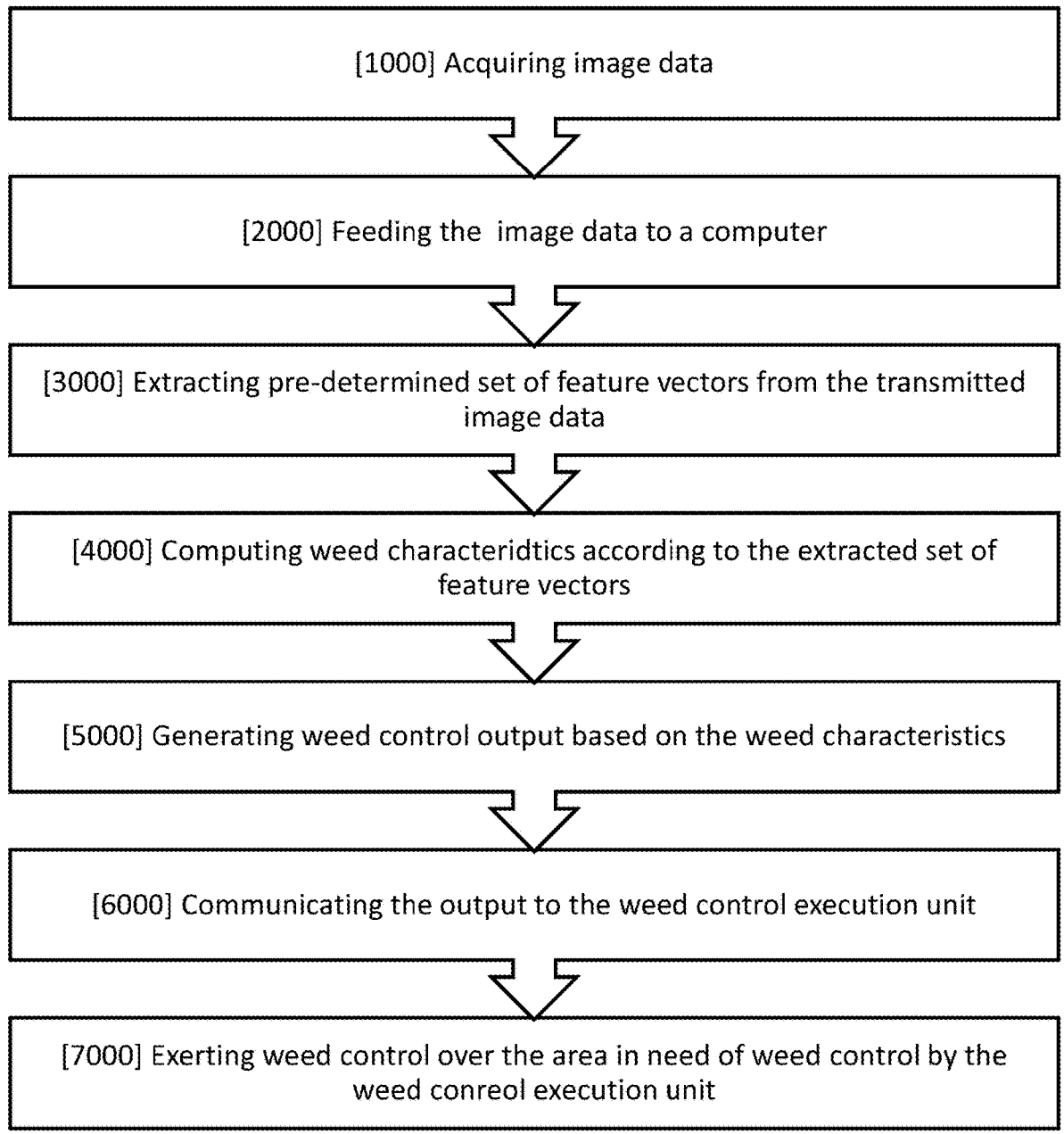
FIG. 4 is illustrating a high-level flowchart of an exemplary embodiment describing a method of real-time weed control in an area where weed control is required, according to some aspects of the current invention.

Reference is now made to FIG. 4 illustrating a schematic flowchart of an exemplary embodiment of a method of real-time weed control in an area where weed control is required, comprising [1000] acquiring an image data 40 of the area by an area scan camera or a line scan camera 100 operatively linked to a vehicle 10 moving along the area 20; [2000] feeding the acquired image data 40 to a computer 50 configured to extract a predetermined set of feature vectors from the image data; [3000] extracting the pre-determined set of feature vectors from the transmitted image data 40; [4000] computing weed characteristics according to the set of feature vectors extracted from said image data; [5000] generating weed control output 60 based on the weed characteristics; [6000] communicating the weed control output 60 to a weed control execution unit 70 operatively linked to the vehicle 10; [7000] exerting the weed control 80 in the area where weed control is required.

Figure 5:
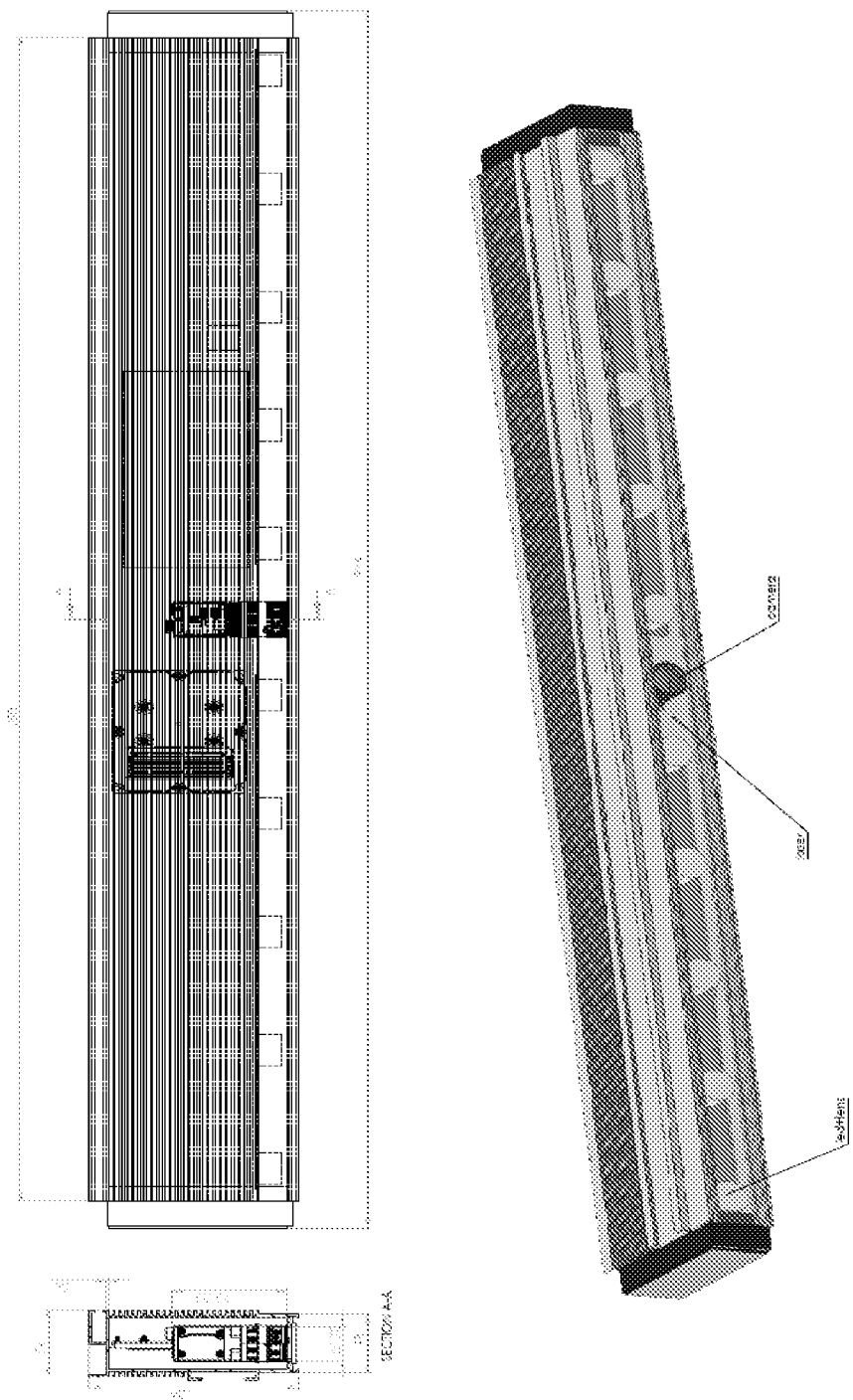
FIG. 5 is photographically presenting an exemplified sensor used in the system and method of the present invention. This figure shows a cross sectional view of modules of an imaging sensor within the scope of the present invention.

Reference is now made to FIG. 5 presenting an exemplified sensor used in the system and method of the present invention. This figure shows a cross sectional view of modules of an imaging sensor within the scope of the present invention. The main modules of the sensor include a camera (e.g. RGB area scan camera) and light sources with pre-defined frequencies, e.g. LED lights with lenses and laser irradiating means. The light sources and camera are preferably positioned within the anterior, preferably lower part of the sensor and are covered by a glass window to enable light transmittance. The sensor further comprises electronic elements, GPU, CPU, along with connections for GPS, speed sensor and WIFI. The electronic type modules are packed in a sealed aluminum profile, preferably in the posterior upper part of the sensor that is used to passively cool the system. The sensor in communicably connected to a computer device comprising a processor, preferably an imaging processor, processing the image data and generating an output enabling identification of the plant or its condition or physiological status in real time. According to specific embodiments of the present invention, the computational device may be based on machine learning algorithms.

FIG. 15 is a table that includes specifications of an imaging sensor as an embodiment of the system and method of the present invention. The imaging sensor can have a profile weight of about 1,500 grams.

Reference is now made to FIG. 6 showing a schematic representation of a block diagram presenting embodiments of the system for real-time plant monitoring and treatment of the present invention. The system includes an input unit providing the signals and power supply which the sensors need for operation. The output signals from the sensors. i.e. image sensor (camera) are transmitted to a computational device containing a processor. According to some embodiments, the computational device records the processed output signals and through a driver/control unit provide instructions to open and close the spraying nozzles.

FIG. 6 shows a system diagram typical for the some embodiments of the invention. The sensor is composed of an image accession unit comprising a camera to facilitate image collection and modulated light source comprised of LED system (e.g. LED PCB) and/or laser diodes (LD) with associated modulated driver and power control electronics. The camera is communicably connected to an input/output interface controller a control unit to communicate the image sensor data to an operator. The control unit comprising a computing module with a central processing unit (CPU) designed for accelerating machine learning applications and applications (e.g. Jetson Xavier). The aforementioned CPU module is communicably connected to GigE Vision and High-Definition Multimedia Interface (HDMI) modules connected to a Network. HDMI switch comprising a router module, preferably including Wifi and Gigf switch and HDMI switch connected to the GigE and HDMI modules, respectively. The CPU (e.g. Jetson Xavier) is further connected to a USB hub module, operably controlling one or more valves (solenoid valves) via one or more Pulse Width Modulation (PWM). The CPU (e.g. Jetson Xavier) is further controlling a speed sensor via Arduino modules.

The light source for the invention may be composed of light emitting diodes. LEDs are crystalline materials composed of various transition elements and dopants that include gallium, arsenic, phosphorous, aluminum, nitrogen and indium. Common material chemistries for LEDs are Gallium Arsenide (GaAs), Gallium Arsenide Phosphide (GaAsP), Gallium Aluminum Arsenide (GaAlAs), Indium Gallium Nitride (InGaN), Gallium nitride (GaN), Indium Gallium Aluminum Phosphide (InGaAlP), and Gallium Phosphide (GaP).

LEDs are available in a number of colors useful for performing plant biomass and pigment measurements. LEDs are available in colors spanning from deep violet (395 nm) to near infrared (940 nm) spectrum. UV LEDs are available in the 350 nm to 370 nm. These devices could be useful for stimulating pigment fluorescence in plants as the spectral distribution for pigment fluorescence in plants spans from 400 nm to 550 nm. Another useful class of LEDs have spectral emissions spanning from approximately 1300 nm to 1550 nm. This range of devices is particularly useful for measuring water stress associated with plants. In addition. LEDs can be easily controlled by sensor controller electronics. It should be obvious that additional detectors can be added to this array.

As will be apparent to those skilled in the art, other methods include the use of averaging techniques, discriminators and direct digital conversion/processing. It is within the scope of the present invention that the method for selective identification and treatment in real-time of a plant or it's environment condition comprises steps of creating a training dataset as described in steps of FIG. 7A-D:

a. Production of plants expressing phenotypic biomarker, preferably visual biomarker detectable by a sensor. The phenotypes are expressed in a constant or inducible pattern, rendering the plant or it's physiological status capable of being selectively identified. The plants can be produced by any method including GMO or non-GMO methods, for example breeding, transformation, genome editing etc. (FIG. 7A).

b. Training of a computational system for identification of the predefined phenotypes, preferably using machine learning/artificial intelligence based algorithms (FIG. 7B).

c. Providing a sensor for identifying the expressed phenotypes in real time. Such sensors include imaging sensors such as RGB camera, camera with NIR and/or IR and/or UV sensor, specific light wavelengths (LED or laser), multispectral or hyperspectral technology, area scan camera or line-scan camera systems or aerial camera or reflectometer, e.g. using Normalized Difference Vegetation Index (NDVI). FIG. 7C presents an exemplified sensor used in the system and method of the present invention. This figure shows a cross sectional view of modules of an imaging sensor within the scope of the present invention. Such modules include an RGB area scan camera 150 located within a front space or cavity or display window 130, LED lights and lenses 140 positioned within an anterior lightning cavity 120, and a posterior cavity 110 with electronics, GPU, CPU, along with connections for GPS, speed sensor and WIFI.

The sensor modules are packed in a sealed aluminum profile in their upper part that is used to passively cool the system. In the lower part of the sensor there is a glass window through which the camera capture images and the illumination wavelengths are transmitted. The sensor modules packaging is essentially waterproof and dust-proof according to IP69K and IP67 standards.

The sensor in communicably connected to a processor, preferably an imaging processor enabling identification of the plant or its condition or physiological status in real time, based on the training of the computational system.

d. The processor communicates the output to the execution unit communicably connected to the sensor, shown in this figure to be operably linked to a mobile system such as an agricultural mobile vehicle (e.g. tractor) for selectively exerting in real-time a predefined treatment such as herbicide spraying, fertilization, irrigation specifically and solely in the area or biosensor plant in need (FIG. 7D). This embodiment shows a target area comprising biosensor plants and plants absent of the biosensor. The vehicle used for applying an agricultural product or treatment to the biosensor plant or its environment, in one embodiment is implemented with the sensor, and is moving along the area: feeding the acquired data to the sensor and performing a responsive selective treatment in real time precisely and explicitly to the biosensor plant or its environment in need. The treatment is customized and designed to complement the biosensor plant or its environment necessities to improve growth and yield of the biosensor crop plant. Elements of the system include sensor array, sensor controller, optionally GPS, fertilizer/herbicide controller, sprayer valves/pumps/actuators and speed sensor. The agricultural product may be either in liquid, gas or solid form and may be, but not limited to, a nutrient, mineral, herbicide or pesticide or fungicide or any other plant treatment or a combination of any of the aforementioned. Such a Variable Rate Application (VRA) or variable rate control system can be mounted to any commercial sprayer or tractor mounted sprayer system. GPS can be incorporated in the system when a map is required for example for plant canopy characteristics for later analysis.

In one exemplary embodiment, the plant treatment means may be a sprayer. e.g. via a solenoid valve control. In yet further embodiment weed control or herbicide, pesticide or fertilizing is exerted by spraying. In yet further embodiment, the spraying is real-time spot-spraying. The "herbicide" refers, but not limited to chemical substances used to control undesired vegetation.

In one embodiment the herbicide is atrazine, terbuthylazine, (S)-metolachlor, metolachlor, terbutryn, simazine, dimethenamid, (S)-dimethenamid, flufenacet, acetochlor, alachlor, isoxaflutole, isoxachlortole, mesotrione, sulcotrione, metosulam, flumetsulam, pendimethalin, bromoxynil, bentazone, carfentrazone-ethyl, clomazone, nicosulfuron, rimsulfuron, halosulfuron-methyl, metribuzin, flumiclorac-pentyl, prosulfuron, primisulfuron-methyl, dicamba, fluthiacet-methyl, pyridate, 2,4-D, clopyralide, diflufenzopyr, fluroxypyr, MCPA, MCPB, mecoprop (MCPP), metobenzuron, thifensulfuron-methyl, aclonifen, EPTC, glyphosate, glufosinate, sulfosate, cyanazine, propaquizafop, metamitron, pyramin, phenmedipham, desmedipham, ethofumesate, triasulfuron, chloridazon, lenacil, triallate, fluazifop, sethoxydim, quizalofop, clopyralide, clethodim, oxasulfuron, acifluorfen, benazolin-ethyl, sulfentrazone, chlorimuron-ethyl, cloransulam-methyl, fomesafen, imazamox, imazaquin, imazethapyr, imazapyr, lactofen, fenoxaprop (P-ethyl), thidiazuron, tribufos, trifluralin, dimethachlor, napropamide, quinmerac, metazachlor, carbetamide, dimefuron, propyzamide, ethametsulfuron-methyl, tebutam, fluometuron, prometryn, norflurazon, pyrithiobac-sodium, MSMA, DSMA, diuron, flurochloridone, dithiopyr, thiazopyr, oxyfluorfen, ethalfluralin, clodinafop, amidosulfuron, diclofop-methyl, diflufenican, ethoxysulfuron, fentrazamide, flazasulfuron, florasulam, fluazolate, flucarbazone, flupyrsulfuron-methyl sodium, flurtamone, iodosulfuron, isoproturon, chlortoluron, chlorsulfuron, metsulfuron-methyl, sulfosulfuron, tribenuron-methyl, 2,4-DB, 2,4-DP, bifenox, flamprop-M, imazamethabenz-methyl, ioxynil, tralkoxydim, fluoroglycofen-ethyl, methabenzthiazuron, isoxaben, prosulfocarb, difenzoquat-metilsulfate, pretilachlor, cinosulfuron, fenclorim, bensulfuron-methyl, imazosulfuron, pyrazosulfuron-ethyl, azimsulfuron, esprocarb, mefenacet, molinate, propanil, pyrazolate, cyhalofop-butyl, bispyribac-sodium, pyriminobac-methyl, cafenstrole, oxadiargyl, oxadiazon, bromobutide, MY-100, dymron, NB 061, MK243, HW-52, AC 014, ametryn, hexazinone, asulam, azafenidin, tebuthiuron, ethametsulfuron-methyl, or a combination thereof.

In the context of the invention, the term "composition" refers but not limited to a formulation of components such as chemical, biological or nutrient components that may additionally comprise at least one component selected from the group consisting of surfactants, solid diluents and liquid diluents, which serves as a carrier. The formulation or composition of ingredients are selected to be consistent with the physical properties of the active ingredient, mode of application and environmental factors such as oil type, moisture and temperature. Useful compositions may include both liquid and solid formulation. Liquid formulations may include solutions (including emulsifiable concentrates), suspensions, emulsions (including micro emulsions, oil-in-water emulsions, flowable concentrates and/or suspoemulsions) and alike, which optionally can be thickened into gels.

In one embodiment of the invention, the composition as described above is useful for selective control of weeds in crops such as wheat, barley, maize, soybean, sunflower, cotton, rice, oilseed rape, sugarcane, citrus, fruit, nut crops, vegetable and grass.

In specific embodiments, the invention yet further provides a method of real-time weed control in an area where weed control is required, comprising: acquiring an image data of the area by a line scan camera operatively linked to a first vehicle moving along the area; feeding the acquired image data to a computer configured to extract a predetermined set of feature vectors from the image data; computing weed characteristics according to the set of feature vectors extracted from said image data and weed control output based on the weed characteristics; communicating the output to a weed control execution unit operatively linked to a second vehicle; exerting the weed control by applying to the area an agricultural composition comprising at least one herbicide. In one embodiment, the first vehicle is a ground vehicle and the second vehicle is an airborne vehicle. In another embodiment, the first vehicle is an airborne vehicle and the second vehicle is aground vehicle.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" or "comprising." when used in this specification, specify the presence of stated features, integers, steps, operations, elements components and/or groups or combinations thereof, but do not preclude the presence or addition of one or more other features, integers, steps, operations, elements, components and/or groups or combinations thereof. As used herein the terms "comprises", "comprising", "includes", "including", "having" and their conjugates mean "including but not limited to". The term "consisting of" means "including and limited to".

As used herein, the term "and/or" includes any and all possible combinations or one or more of the associated listed items, as well as the lack of combinations when interpreted in the alternative ("or").

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and claims and should not be interpreted in an idealized or overly formal sense unless expressly so defined herein. Well-known functions or constructions may not be described in detail for brevity and/or clarity.

It will be understood that when an element is referred to as being "on," "attached" to, "operatively coupled" to, "operatively linked" to, "operatively engaged" with, "connected" to, "coupled" with, "contacting," etc., another element, it can be directly on, attached to, connected to, operatively coupled to, operatively engaged with, coupled with and/or contacting the other element or intervening elements can also be present. In contrast, when an element is referred to as being "directly contacting" another element, there are no intervening elements present.

It will be understood that, although the terms first, second, etc., may be used herein to describe various elements, components, regions, layers and/or sections, these elements, components, regions, layers and/or sections should not be limited by these terms. Rather, these terms are only used to distinguish one element, component, region, layer and/or section, from another element, component, region, layer and/or section.

Certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

All publications, patent applications, patents, and other references mentioned. The disclosures of these publications in their entireties are hereby incorporated by reference into this application in order to more fully describe the state of the art to which this invention pertains. In case of conflict, the patent specification, including definitions, will prevail. In addition, the materials, methods, and examples are illustrative only and not intended to be limiting. Throughout this application various publications, published patent applications and published patents are referenced.

It will be appreciated by persons skilled in the art that the present invention is not limited to what has been particularly shown and described hereinabove. Rather the scope of the present invention is defined by the appended claims and includes both combinations and sub-combinations of the various features described hereinabove as well as variations and modifications thereof, which would occur to persons skilled in the art upon reading the foregoing description.

In order to understand the invention and to see how it may be implemented in practice, a plurality of preferred embodiments will now be described, by way of non-limiting example only, with reference to the following examples.

Example 1

A System for Real Time Treatment of a Plant or its Environment Condition

This example describes an exemplified embodiment of the present invention. In connection to the phenotypic biosensors described inter alia, a system which includes a set of plant treatment modules designed to be installed along a farming implement vehicle (according to one embodiment, the modules are installed such that they are located one next to the other along an axis that is perpendicular to the movement axis of the vehicle (see FIG. 6D). This figure photographically presents an agricultural ground vehicle or machinery or equipment to be implemented with one or more sensors and/or treatment modules, according to some embodiments of the present invention.

Each treatment module includes the following: (i) an imaging sensor such as RGB camera, multispectral, hyperspectral, visible light frequency range, near infrared (NIR) frequency range, infrared (IR) frequency range, and combinations of the aforementioned, (ii) an illumination source, and (iii) a controller adapted to control an execution unit, for example weeding unit such as an herbicide sprayer. The imaging sensor is communicably connected to a processing device, such as a computer (e.g. a GPU) responsive to the module. The processing device is communicably connected to the controller. The outputs of the imaging sensor are processed by the processing device and executing using a machine learning model. The processing device instructs the controller to operate according to the outcome of the execution unit. Each of the treatment modules is operated independently from other treatment modules to control the operation of the respective execution unit while the vehicle with the farming implement is moving along the agriculture area.

In preferred embodiments, in each of the treatment modules, image data received by the imaging sensor (e.g. the respective RGB camera) is processed in real time (while the vehicle with the farming implement is moving along the agriculture area) to form feature vector(s). The feature vector(s) are fed by the respective processor into a machine learnt model (i.e. neural network) and the output of this model (inference phase) are used to predict and determine the operation of the execution unit (e.g. weeding unit).

Example 2

The example provides a system comprising a series of opto-electronic sensors for detecting predesigned plant biosensors, scanning the surface, optionally velocity sensors, a computational device for data processing, and herbicide sprayers or other plant treatment application modules operably linked to the sensors. In specific embodiments, unlike other selective spraying systems, the sensors do not employ the reflectance properties of the plant, but the fluorescence properties.

Such sensors can be designed (by selecting spectral frequencies of the sensor capable of detecting plants modulated expression of selected spectral properties indicative of the plant status or condition) for weed detection, and further for a wide variety of plant conditions.

It should be acknowledged that selective herbicide or fertilizers spraying, based on plants expressing biosensor genes with detectable phenotypic characteristics leads to considerable savings on herbicide or fertilizer use because it is only applied at spots or areas or specific plants in need, which are easily distinguished by the sensors. The present invention achieves automated selective spraying which is significantly cost effective.

In a specific example, a weed, or other crop with predefined phenotypic characteristic, sensor can be made by combining a visible light emitting source and a detector which is sensitive in the NIR and not in the visible part of the spectrum. Because ambient light should not affect the performance of the sensor, the light emitter should not emit continuous light but pulsed or other periodically modulated light. Then an electronic filter can isolate the fluorescence signal from (not modulated) NIR components in the ambient light. Because the sensor has to be fast, the visible light source should be modulated at a frequency significantly above about 30 Hz, such as lasers, low pressure plasma lamps and LEDs. To achieve sensitivity, the light source should be with relatively high light intensity.

In this example, the sensor uses the chlorophyll fluorescence effect in weeds or plants. Therefore, surface reflective properties, which may cause difficulties for weed sensors based on the reflection principle, are herein minimized. In the sensor inter alia described, optically filtered LEDs provide the chlorophyll excitation source. NIR emission from chlorophyll is detected by photodiodes. Ambient light is rejected using optical and electronic filtering techniques. The sensitivity of the sensor (e.g. weed sensor) can be increased by (partly) shielding the sensor from ambient light.

In addition to the sensors, the system of the present invention may contain plants expressing predesigned biosensors, velocity sensors, an input unit, a computational unit, a valve driver unit and a herbicide/fertilizer spraying system. Such a system can on the one hand detect and selectively spray small weed seedlings of about 10 mm2 in full ambient light, and on the other hand can distinguish between undesirable weeds, and desirable crops such as corn or wheat expressing modulated specific spectral properties which can be selectively identified by the sensors in real time. In both cases selective spraying can be applied by an execution unit operably linked to the sensor and/or computational unit.

Example 3

This example presents some of the optional applications of the herein disclosed system and method for plant monitoring and treatment in real time:

A System for Real Time Selective Cereal Weeds Control in Wheat

The Problem to be Solved:

The wheat cereal weeds herbicides are expensive and polluting the environment. A considerable percentage of their usage can be saved by selective spraying only where there are weeds from the cereal family. The problem was that many weeds in the cereal family are very similar in their visual appearance to wheat, especially in the early stages of the crop where the spraying is carried out. Even an expert agronomist cannot always distinguish the wheat from some of the weed species just by looking at the plants from above. Therefore, it is very difficult to train a system that separates the wheat from the cereal weed in an efficient way, allowing for selective spraying.

The Solution Provided by the Present Invention:

The present invention provides a wheat strain that expresses a high concentration of anthocyanins in the early developmental stages, which changes its color to red type and significantly facilitates and improves its separation from the other weeds. Anthocyanins are naturally expressed in wheat in certain stress conditions. It is within the scope of the present invention that by genome editing, a new wheat strain is produced which accumulates anthocyanins in excess in leaves in early developmental stages of the plant and thus express a reddish color phenotype in early growth stages of the crop. A tagged image library or pool is then generated and used for training (e.g. using machine learning algorithms) predestined algorithms to distinguish it from the other cereals—an easy task in this situation where the leaves are red, but almost impossible when this phenotype does not exist.

It should be noted that without the unique phenotype, the inventors were unable to reach a percentage of separation greater than 50% and with this technique, combined with the system and method of the present invention as herein described, over 50%, specifically about 90% identification and separation between the wheat crop and other undesirable weeds could be reached, a separation value which is needed for extensive agricultural application. The technological solution of the present invention enable selectively spraying in the field using the system for real-time monitoring and treatment of plants, trained to selectively identify the new phenotype and not spray the wheat, but only spraying the cereal weeds.

A System for Real Time Selective Nitrogen Fertilization in Wheat

The Problem to be Solved:

As of today, the whole field or agricultural area is sprayed or fertilized with nitrogen evenly though different plants need different levels of nitrogen. There is currently no clear phenotype that can be detected using a standard RGB camera which will allow the assessment of the level of nitrogen in wheat plants in order to make a selective spraying or fertilization and provide the amount of nitrogen per plant as actually needed.

The Solution Provided by the Present Invention:

The current invention provides a wheat strain or variety that expresses a waxy phenotype, namely deposition of cuticular β-diketone wax on their surfaces, in response to a nitrogen deficiency. The waxy phenotype casing changes the absorption frequencies of wheat. The present invention is aimed to show that by training the system herein disclosed (e.g. using machine learning algorithms) to distinguish between wheat with and without the waxy phenotype. In this way, the nitrogen status in wheat, which is designed to be associated with the waxy cuticle phenotype, can be easily identified, a task nearly impossible today.

A System for Real Time Selective Nitrogen Fertilization in Corn

The Problem to be Solved:

Until the present invention, the whole field or agricultural area is sprayed or fertilized with nitrogen evenly though different plants need different levels of nitrogen. There is currently no clear phenotype that can be detected using a standard RGB camera which will allow the assessment of the level of nitrogen in corn plants in order to make a selective spraying or fertilization and provide the amount of nitrogen per plant as actually needed.

The Solution Provided by the Present Invention:

It is herein acknowledged that under phosphorus stress, an accumulation of anthocyanins appears at the leaf edges—this is relatively easy phenotype for a machine learning system to identify. The present invention achieves a corn variety that expresses such a phenotypic visual characteristic in nitrogen deficiency conditions of the plant and thus enable selective spraying of nitrogen in real time, using the system herein disclosed, a task nearly impossible up until now.

Early detection of *Orobanche* (broomrape or broom-rape) parasitization in tomato The Problem to be Solved:

The *Orobanche* parasitic plant attaches to the tomato roots, causing it damage and significant losses in crop yields. The problem is that it is not possible to detect *Orobanche* prior to its germination above the ground, so there is no way to perform a selective spray against *Orobanche*, namely, spraying only where it exists.

The Solution Provided by the Present Invention:

When *Orobanche* attaches to the tomato roots, it exudates specific molecules, i.e. terpenoid lactone molecules, for example, germination stimulants of strigol-related compounds. It is within the scope of the current invention to develop tomato plants accumulating anthocyanins in the leaves in response to the exudate molecule secreted by the parasitic plant. This enables selective control and prevention of parasitic plants in the field using the system for real-time monitoring and treatment of plants expressing phenotypic visual marker responsive to a plant undesirable condition.

Further examples of applications of the herein disclosed plant bio-sensing system include, but are not limited to:

Early detection of Northern Corn Leaf Blight leaf disease in corn.

Early detection of infestation of the corn rootworm larvae of corn roots.

Detection of a soybean disease with expression of a fluorescent protein.

Detection of a virus in sugar beet coupled to expression of butylin.

Detection of water stress in melons and watermelons by phytoene synthase visual marker expression.

Example 4

Nitrogen Sensing and Management in Maize

This example provides N-biosensor-corn plant and a system for spot fertilizing nitrogen in corn, preferably by using leaf morphology as a biosensor trait.

As described above, the system of the present invention is capable of snapping images in 25 kph and analyze them in real-time.

Project Aim:

Detecting corn-plant nitrogen status by RGB images in a robust and applicable way.

Objectives:

1 Developing corn varieties, preferably commercial varieties, implemented by leaf color biomarker capable of sensing nitrogen deficiency.

2 Developing a sustainable solution for nitrogen fertilizing by using biosensor-corn-seeds in combination with a real time spot fertilizing technology.of the present invention.

The rational—The developed corn-N-biosensor varieties grown for commercial use will be subjected to spot nitrogen fertilization as needed, by using the spot spraying systems of the present invention.

The present invention (e.g. the present example) provides a sustainable solution for nitrogen fertilization by breeding biosensors corn seeds. These biosensor-corn-plants are produced such that they are capable of changing their phenotype when a threshold of nitrogen deficiency is reached. The phenotype change can be detectable with the optical system of the present invention (described above) that is able to send a signal to spot fertilize the relevant plants.

Reference is now made to FIG. 12, schematically describing embodiments of the method and system of the present invention. A selected crop, such as corn is modified by breeding/genome editing/DNA modification to express a visual marker/biomarker/reporter gene associated with a promoter sensitive to N deficiency. The visual marker is expressed/activated in N deficiency conditions.

The biosensor-corn-plants were produced using genome editing techniques. It is noted that the skilled person will know that any relevant genome editing technique known in the art can be used, for example, clustered regularly interspaced short palindromic repeats and CRISPR-associated protein (CRISPR-Cas), transcription activator-like effector nucleases (TALENs), meganucleases and zinc-finger nucleases (ZFNs). The genome editing tools are herein used for precise targeted promotor replacement by integration of a selected promotor into a specific genomic location through homology-directed repair (HDR).

The promoter is responsive to a selected physiological condition of the plant that requires monitoring, such as nitrogen concentration or level in the plant. The promoter is introduced into a genomic location to be operably linked to a preselected reporter endogenous gene (biomarker), such as leaf color or morphology.

The methods used for transformation and generating of the biosensor plants include, but are not limited to:

Particle bombardment of mature embryos

The reporter genes and promotors involved in the phenotype development and introduced into the plant for replacement of endogenous genes/promoters, will be native (cisgenic).

In preferred embodiments, the generated plant will not be considered a genetically modified plant in terms of regulation, i.e. in the US.

Candidate reporter genes within the scope of the present invention include:

(a) Yellow stripe—ys1, ys3 ('Yellow stripe' phenotype is shown in FIG. 8)
(b) Old Gold Stripe—og1 ('Old Gold Stripe' phenotype is shown in FIG. 9)
(c) Brown midrib—bm1, bm2, bm3 ('Brown midrib' phenotype is shown in FIG. 10)

An example of a candidate promotor used in corn for sensing nitrogen deficiency is the amino acid glutamine (Gln) promotor.

Gln1 gene encodes an isoform of GS1 (Glutamine synthetase) suggesting that this isoform, may be induced in response to N deficiency.

Reference is now made to FIG. 11, presenting schematic representation depicting expression and possible function of Glutamine Synthetase (GS) isoforms or isoenzymes within maize (see Martin et al., Two Cytosolic Glutamine Synthetase Isoforms of Maize Are Specifically Involved in the Control of Grain Production, The Plant Cell, Vol. 18, 3252-3274, 2006, incorporated herein by reference). In this figure Gln1-1 to Gln 1-5 are the five genes encoding cytosolic GS and Gln2 the gene encoding plastidic GS. Their tissue or cellular localization is indicated in red, and their putative function is indicated in blue, deduced from the analysis of the gln1-3- and gln1-4-deficient mutants. The large red arrows indicate the flux of Gln occurring within the plant: 1, from the roots to the shoots (reaction catalyzed by GS1-1); 2, in the phloem (reaction catalyzed by GS1-2); 3, from the source leaves to the ear (reaction catalyzed by GS1-3 and GS1-4); and 4, from the young leaves to the other shoot parts (reaction catalyzed by GS2). The function of GS1-5 is not determined, as indicated by question marks.

With respect to Gln1-1, it is herein acknowledged that Gln1-1 transcripts are less abundant as compared with that of Gln3 and Gln4 and mostly present in N deficiency plants, regardless of the leaf developmental stage.

With respect to Gln1-2, it is herein acknowledged that by expression of the Gln1-2 promotor/GUS heterologous construct, no expression in leaves and roots was detected.

With respect to Gln1-3 and Gln1-4, it is herein acknowledged that Gln1-3 and Gln1-4 are highly expressed regardless of the leaf age and the level of fertilization.

With respect to Gln2, it is herein acknowledged that the expression of the Gln2-Gln1-5 is primarily at early stages and in green tissue in leaf blade.

Reference is now made to FIG. 13, schematically presenting exemplified elements of the N-biosensor corn plants of the present invention. These elements include:

Gln 1-1 promotor: Gln1-1 transcripts mostly present in Corn plants regardless of the leaf developmental stage. Gln1 gene encodes a different isoform of GS1 (Glutamine synthetase) suggesting that this isoform, may be induced in response to N deficiency.

REFERENCE IS NOW MADE TO AN EMBODIMENT IN WHICH

Candidate reporter genes: genes expressing leaf color/leaf veins/margins coloration phenotype, for example, Yellow stripe-ys1, ys3, Old Gold Stripe-og1 and Brown midrib-bm1, bm2, bm3.

Candidate regulatory regions: promoter regions of Gln1 gene isoforms Gln1-1, Gln1-2, Gln1-3 or Gln1-4 induced in response to N deficiency in the plant.

The N-biosensor corn plants comprising the above DNA construct (i.e. generated by genome editing within the plant), produce a detectable phenotype associated with N deficiency.

According to further aspects of the present invention, different elite corn lines for each maturation zone are characterized by a unique phenotypic expression (N-biosensor trait) that allows identification by an appropriate sensor system.

Thus according to a main embodiment of the present invention, the genetic system or construct within the plant, "senses" the state of nitrogen in the plant and allows the grower to operate accordingly in real time.

It is emphasized that the N-biosensor trait/DNA construct has no negative effect on corn yield quantity and/or quality.

According to a further aspect, the N-biosensor corn plant of the present invention is capable of "sensing and reporting" the nitrogen status in a field comprising the N-biosensor corn plants (e.g. at a percentage of at least 5-10% of the plants in the crop field or agricultural area) and thus provides the grower with a real time system that monitors the requirement for nitrogen fertilization or supplemental nitrogen application in a given field.

By using a system capable of imaging, analyzing and classifying in real time the relevant plant phenotypes of the N-biosensors corn plants (e.g. leaf color/leaf veins/margins coloration), precision application of nitrogen fertilizer can be performed.

In general, the biosensor plant development process includes producing corn varieties sensing and reporting nitrogen deficiency by operably linking promoters of genes sensitive to nitrogen status in the crop to a reporter gene such as leaf color biomarker. This provides a sustainable solution for nitrogen fertilization.

In some embodiments, the N-biosensor corn plants are developed for commercial use and therefore has a genetic background of commercially used varieties.

The expression of the genes controlling the selected plant phenotypic trait (e.g. leaf veins/margins coloration) in corn is modified using genome editing technique.

It is noted that the expression of the genes for nitrogen sensing is not affected by the leaf/plant developmental stage.

The method used for generating the N-biosensor corn plants is genome editing for precise targeted promotor replacement. The desirable N-sensitive promoter is integrated by targeted genome editing into a regulatory region of a preselected reporter gene (such as a gene involved in leaf morphology) through homology-directed repair (HDR). The gene and the promotor selected for generating the construct for phenotype development (promoter replacement) are native (cisgenic).

Nitrogen precise application can be performed by spot spraying, satellites or by obtaining soil samples or leaf samples. Mainly urea is used for fertilization.

In another embodiment, application from a self-propelled sprayer is used.

Reference is now made to Table 3, presenting differences between the system of the current invention comprising the biosensor crop plants (e.g. N-biosensor plant) Vs NDVI based sensors (absent of the usage of biosensor crop plants).

TABLE 3

Comparison between the system and method of the present invention and NDVI based sensors

| Feature | System using N-Biosensores | NDVI based sensors |
| --- | --- | --- |
| Difficulty of use | Plug and play | Need Calibration in every use, including growing reference rows. |
| N stat detection accuracy | Very accurate | Not so accurate |
| Robustness | Not effected from different plant stress | Can be effected from many biotic and a-biotic stresses |
| Weather effected | Not effected | Effected from fog, dew, shading etc. |
| Relevance to application date of the plant N-stat | 2 days ago | ~10 days |
| Spot spraying resolution | Up to the plant level | 10-100+ (m^2) |
| Help scouting | Yes, farmer can see the plant N-stat in the field before the application | No, farmer can not know how much nitrogen will be applied |

To summarize, the N-biosensor plants in combination with a computerized sensing and treating system of the present invention provides an accurate and high value solution for selective crop management in real time. The biosensor seeds can be distributed in a crop field providing valuable information in real time on the status of various important parameters of the plant or its environment condition, enabling selective monitoring and management of the crop (i.e. selective fertilization or weed control) in real time.

Example 5

Mixed Field Approach for Using the Biosensor Plants of the Present Invention

In this example, the biosensor plants of the present invention are mixed with or distributed in proximity to crop varieties, lines or strains, preferably commercial crop varieties, lines or strains, absent of the biosensor trait encoded by at least one modified genomic locus, grown in the same field or agricultural area (e.g. the biosensor plants are at a percentage of at least 5-10% of the plants in the crop field or agricultural area). Thus, there is no need for converging all elite lines/hybrids into modified biosensor plants carrying the endogenously created construct of a biosensor promoter and a reporter gene.

In this approach, for example, the N-biosensor plant, strain or variety is used to sense nitrogen level in a field containing commercially valuable crop lines. Then, spot nitrogen fertilization is applied to the field in precise amounts and to the plants in need by using suitable sensors with AI technology combined with spot spraying capabilities.

It is within the scope of the present invention that the biosensor plants are crop plants species or varieties such as corn, vegetables, wheat etc. or are cover cop plant types such as rye (also known as winter rye or cereal rye), Buckwheat, Clover, Sorghum, Hairy vetch, Legumes and Brassicas.

As shown in FIG. 14, N-biosensor seeds are randomly distributed in the field, e.g. biosensor varieties are mixed with commercial variety, preferably, of the same species. The status of these biosensor plants is detected in real time (via expression of the visual marker) by suitable sensors, sending a signal to an execution unit to exclusively spray/fertilize the area where spraying/fertilization is required.

REFERENCES

Martin, et al., Two Cytosolic Glutamine Synthetase Isoforms of Maize Are Specifically Involved in the Control of Grain Production. The Plant Cell November 2006, 18 (11) 3252-3274.

Hen-Avivi, S. et al., A metabolic gene cluster in the wheat W1 and the barley Cer-cqu loci determines β-diketone biosynthesis and glaucousness. The Plant Cell June 2016, 28 (6) 1440-1460.

He, X. et al. The nitrate-inducible NAC transcription factor TaNAC2-5A controls nitrate response and increases wheat yield. Plant Physiology November 2015, 169 (3) 1991-2005.

Jeewani, D. C. & Hua, W. Z. Recent Advances in Anthocyanin Biosynthesis in Colored Wheat. Research Journal of Biotechnology June 2017, 12 (6) 57-62.

Takei, K., et al., Nitrogen-dependent accumulation of cytokinins in root and the translocation to leaf: Implication of cytokinin species that induces gene expression of maize response regulator. Plant and Cell Physiology January 2001, 42, Issue 1, 15, 85-93.

Holton, T. A. & Cornish, E. C. Genetics and biochemistry of anthocyanin biosynthesis. Plant Cell. July 1995, 7 (7) 1071-1083.

Calderon-Vazquez, C., et al., Transcript profiling of Zea mays roots reveals gene responses to phosphate deficiency at the plant- and species-specific levels. Journal of Experimental Botany June 2008, 59 (9) 2479-2497.

Campbell W. H., Molecular Control of Nitrate Reductase and Other Enzymes Involved in Nitrate Assimilation. In:

Foyer C. H., Noctor G. (eds) Photosynthetic Nitrogen Assimilation and Associated Carbon and Respiratory Metabolism. Advances in Photosynthesis and Respiration, 2002, 12. Springer, Dordrecht.

Gowri, G. et al., Nitrate reductase transcript is expressed in the primary response of maize to environmental nitrate. Plant Molecular Biology 1992, 18 55-64.

Shaner, D. L. & Boyer, J. S. Nitrate reductase activity in maize (Zea mays L.) leaves: I. Regulation by nitrate flux. Plant Physiology October 1976, 58 (4) 499-504.

Konishi, M. & Yanagisawa, S. The regulatory region controlling the nitrate-responsive expression of a nitrate reductase gene, NIA1, in Arabidopsis. Plant and Cell Physiology May 2011, 52 (5) 824-836.

What is claimed is:

1. A system for selective crop management, comprising:
an agricultural vehicle;
one or more image sensors mounted on the agricultural vehicle, the one or more image sensors configured to acquire an image of a respective region of an agricultural field along a direction of travel of the agricultural vehicle, the respective region including a genetically modified plant configured to modify a visual characteristic of at least a portion of the genetically modified plant in response to a predetermined physiological state of the genetically modified plant, the genetically modified plant having a first state in which the visual characteristic is unmodified and the genetically modified plant does not have the predetermined physiological state, and a second state in which the visual characteristic is modified and the genetically modified plant has the predetermined physiological state;
a selective sprayer mounted on the agricultural vehicle;
a computer on the agricultural vehicle, the computer including at least a processor circuit and non-transitory memory, the processor configured to:
detect a state of the genetically modified plant represented in the image using a trained machine learning (ML) model stored in the non-transitory memory, the training ML model having been trained with first images that include one or more genetically modified plants in the first state and second images that include one or more genetically modified plants in the second state;
produce a trigger signal that causes the selective sprayer to spray the respective region of the agricultural field when the second state is detected.

2. The system of claim 1, wherein the predetermined physiological state comprises a predetermined developmental state, a predetermined photosynthesis, a predetermined respiration status, a predetermined plant nutrition status, a predetermined plant hormone functional status, a predetermined tropism, a predetermined nastic movement, a predetermined photoperiodism, a predetermined water state, a predetermined abiotic stress, a predetermined biotic stress, a predetermined vegetative index, a predetermined plant chlorophyll content, a predetermined plant pigment content, a predetermined nitrogen content, a predetermined phosphorus content, a predetermined potassium content, a predetermined micronutrient content, a predetermined secondary content, and/or a disease state.

3. The system of claim 1, wherein the visual characteristic comprises a spectral property of the genetically modified plant.

4. The system of claim 3, wherein the spectral property includes an absorbance property and/or a reflectance property.

5. The system of claim 3, further comprising one or more light sources mounted on the agricultural vehicle, the one or more light sources configured to emit light having at least one predetermined wavelength onto the respective region of the agricultural field, the at least one wavelength corresponding to the spectral property of the genetically modified plant.

6. The system of claim 1, wherein:
the predetermined physiological state comprises a deficiency in a plant nutrient, and
the selective sprayer is configured to spray the respective region of the agricultural field with the plant nutrient when the second state is detected.

7. The system of claim 1, wherein the trained ML model is trained to generate an output based on predetermined feature vectors extracted from the first and second images.

8. The system of claim 1, wherein the one or more image sensors comprise one or more reflectometers.

9. A system for real-time monitoring of plants, comprising:
one or more image sensors configured to acquire image data of a biosensor plant having a visual biomarker representing a predefined phenotype of the biosensor plant; and
a computer that receives as an input the image data from the one or more image sensors, the computer including at least a processor circuit that is configured to:
detect an expression of the visual biomarker in the biosensor plant represented in the image data, and
output one or more control signals that cause a selective sprayer to selectively spray an agricultural product onto a target area that includes the biosensor plant when the visual biomarker is expressed.

10. The system of claim 9, wherein the selective sprayer is mounted on an agricultural vehicle.

11. The system of claim 9, wherein the one or more image sensors is/are configured to detect light having one or more wavelengths that correspond to the expression of the visual biomarker.

12. The system of claim 9, wherein the processor circuit that is configured to detect the visual biomarker using a trained machine-learning model that was trained with first and second training images of plants, the first training images including the expression of the visual biomarker, the second training images not including the expression of the visual biomarker.

13. The system of claim 9, wherein the visual biomarker is encoded by a preselected reporter gene allele having the predefined phenotype, the preselected reporter gene allele operably linked to a regulatory region of a preselected gene allele that is responsive to at least one parameter or condition of the biosensor plant and/or its environment such that an expression of the predefined phenotype is indicative of a status of said at least one parameter or condition of the biosensor plant and/or its environment.

14. The system of claim 9, wherein the predefined phenotype is expressed in response to a predetermined physiological state of the biosensor plant.

15. The system of claim 9, wherein the agricultural product comprises an herbicide, a pesticide, a fertilizer, and/or an irrigation.

16. The system of claim 9, further comprising one or more light sources that emit light having at least one predetermined wavelength onto a target area, the at least one predetermine wavelength corresponding to the visual biomarker.

17. A system for real-time monitoring of plants, comprising:
- one or more light sources that emit light having at least one predetermined wavelength onto a target area that includes a genetically modified plant configured to express a spectral property indicative of at least one parameter or condition of the genetically modified plant or its environment condition;
- one or more light detecting sensors configured to detect image data representing the genetically modified plant in the target area; and
- a computer that receives as an input the image data from the one or more light detecting sensors, the computer including at least a processor circuit that is configured to:
    - analyze the image data to determine whether the spectral property is expressed, and
    - output one or more control signals that cause a selective sprayer to selectively spray an agricultural product onto the target area when the spectral property is expressed.

18. The system of claim 17, wherein the spectral property comprises an absorbance, a reflectance, and/or a fluorescence.

19. The system of claim 17, wherein the processor circuit is configured to analyze the image data using a trained machine-learning model that was trained with first and second training images of plants, the first training images including an expression of the spectral property, the second training images not including the expression of the spectral property.

20. The system of claim 17, further comprising:

an agricultural machine; and the selective sprayer, wherein the one or more light sources, the one or more image sensors, the computer, and the selective sprayer are mounted on and/or included in the agricultural machine.

* * * * *